US012644076B2

(12) United States Patent
Herrmann et al.

(10) Patent No.: US 12,644,076 B2
(45) Date of Patent: Jun. 2, 2026

(54) PERFUME SYSTEM FOR PERFUMED CONSUMER PRODUCT

(71) Applicant: Firmenich SA, Satigny (CH)

(72) Inventors: Andreas Herrmann, Satigny (CH); Alain Trachsel, Satigny (CH); Damien Berthier, Satigny (CH); Nicolas Paret, Satigny (CH)

(73) Assignee: FIRMENICH SA, Satigny (CH)

( * ) Notice: Subject to any disclaimer, the term of this patent is extended or adjusted under 35 U.S.C. 154(b) by 686 days.

(21) Appl. No.: 17/801,781

(22) PCT Filed: Apr. 22, 2021

(86) PCT No.: PCT/EP2021/060511
§ 371 (c)(1),
(2) Date: Aug. 23, 2022

(87) PCT Pub. No.: WO2021/214205
PCT Pub. Date: Oct. 28, 2021

(65) Prior Publication Data
US 2023/0093639 A1 Mar. 23, 2023

(30) Foreign Application Priority Data
Apr. 24, 2020 (EP) .................................... 20171256

(51) Int. Cl.

| | |
|---|---|
| ***C11D 3/50*** | (2006.01) |
| ***A61K 8/11*** | (2006.01) |
| ***A61K 8/35*** | (2006.01) |
| ***A61Q 13/00*** | (2006.01) |
| ***C11B 9/00*** | (2006.01) |

(52) U.S. Cl.
CPC ................ *C11D 3/505* (2013.01); *A61K 8/11* (2013.01); *A61K 8/35* (2013.01); *A61Q 13/00* (2013.01); *C11B 9/0015* (2013.01); *A61K 2800/412* (2013.01); *A61K 2800/56* (2013.01); *A61K 2800/81* (2013.01)

(58) Field of Classification Search
CPC ......... C11B 9/0015; A61Q 13/00; A61K 8/11; A61K 8/35; A61K 2800/56; A61K 2800/412; A61K 2800/81; C11D 3/505
USPC .......................................................... 512/4, 1
See application file for complete search history.

(56) References Cited

U.S. PATENT DOCUMENTS

| | | | | |
|---|---|---|---|---|
| 2014/0275288 | A1 | 9/2014 | Herrmann et al. | |
| 2014/0323376 | A1* | 10/2014 | Berthier .................. | B01J 13/16 512/4 |
| 2016/0108346 | A1 | 4/2016 | Herrmann et al. | |
| 2016/0120773 | A1 | 5/2016 | Herrmann et al. | |
| 2017/0266103 | A1 | 9/2017 | Herrmann et al. | |

FOREIGN PATENT DOCUMENTS

| | | | |
|---|---|---|---|
| WO | 2013/050303 | A1 | 4/2013 |
| WO | 2013/079435 | A1 | 6/2013 |
| WO | 2014/187833 | A1 | 11/2014 |
| WO | 2014/187874 | A1 | 11/2014 |
| WO | 2016/083321 | A1 | 6/2016 |

OTHER PUBLICATIONS

Paret et al, Controlled Release of Encapsulated Bioactive Volatiles by Rupture of the Capsule Wall through the light-Induced Generation of a Gas, 2015, Angew. Chem. Int. Ed., 54, 2275-2279 (Year: 2015).*

Paret et al, Developing Multi Stimuli-Responsive Core/Shell Microcapsules to Control the Release of Volatile Compounds, 2019, Macromol. Mater. Eng., 304, 1800599 (Year: 2019).*

* cited by examiner

*Primary Examiner* — Jessica Whiteley

(57) ABSTRACT

The present invention relates to a perfume system comprising a core-shell microcapsule A, optionally, a core-shell microcapsule B, and optionally, a free perfume oil, wherein the core of the core-shell microcapsule A and/or the free perfume oil comprises a 2-oxoacetate derivative of formula (I) as well as a perfumed consumer product comprising the same and methods and uses of the same for enhancing, conferring, increasing and/or modifying the fragrance properties and/or the fragrance intensity of perfumed consumer products.

15 Claims, 1 Drawing Sheet

PERFUME SYSTEM FOR PERFUMED CONSUMER PRODUCT

This present application is a U.S. national phase entry under 35 U.S.C. § 371 of PCT Application No. PCT/EP2021/060511, filed Apr. 22, 2021, which claims priority to European Patent Application No. 20171256.9, filed Apr. 24, 2020. The entire contents of these applications are explicitly incorporated herein by this reference.

TECHNICAL FIELD

The present invention relates to a perfume system comprising a core-shell microcapsule A, optionally, a core-shell microcapsule B, and optionally, a free perfume oil, wherein the core of the core-shell microcapsule A and/or the free perfume oil comprises a 2-oxoacetate derivative of formula (I) as well as a perfumed consumer product comprising the same and methods and uses of the same for enhancing, conferring, increasing and/or modifying the fragrance properties and/or the fragrance intensity of perfumed consumer products.

BACKGROUND OF THE INVENTION

One of the problems faced by the perfumery industry lies in the relatively rapid loss of the olfactive benefit provided by odoriferous compounds as a result of their volatility, particularly that of "top-notes". Some fragrance ingredients can be also unstable in applications of functional perfumery and get lost due to degradation or to rapid evaporation. These problems are often tackled through the use of delivery systems, e.g. capsules containing a perfume, to release the fragrance in a controlled manner. Encapsulation of the fragrance can at least partially solve the evaporation problem, but many types of microcapsules are known to lose parts of the fragrance during storage via diffusion through their shells or walls or as a result of the nature of the consumer product into which they are incorporated and which contains surface active ingredients capable of causing leakage of the perfume. To minimize perfume leakage, the crosslinking of the capsule wall might be increased. However, to perceive the perfume with such systems, one either needs to mechanically break the microcapsules or to generate a spontaneous leakage of the perfume out of the capsules at the desired time. In the first case, the olfactive experience is limited to scratching episodes, while in the second case one usually encounters problems of performance due to issues related to the limited shelf-life of the consumer product containing the microcapsules.

It is therefore desirable to create new perfume systems capable of solving or at least reducing the above-cited problems.

It is also desirable to improve the performance of for example light-induced fragrance release and the light-induced expansion or cleavage of the capsule wall of the perfume system.

It is also desirable to provide creation rules for perfume systems which allow improving the performance of such systems.

The present invention provides solutions to overcome the above-mentioned disadvantages associated with the known perfume compositions and, in particular, improve the performance of perfume systems.

DETAILED DESCRIPTION OF THE INVENTION

Figure 1:
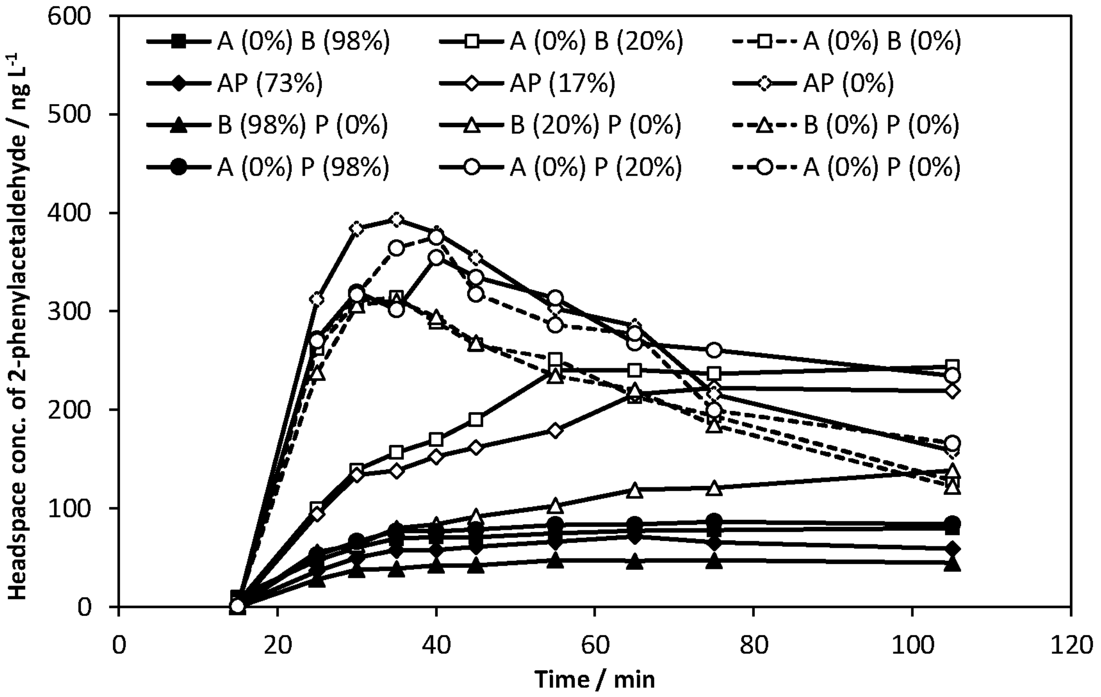
FIG. 1: Dynamic headspace concentrations of 2-phenylacetaldehyde generated from 2-phenylethyl 2-oxo-2-phenylacetate (O1) according to formula (I) upon photoirradiation of different perfume systems containing various amounts of perfumery raw materials of Group B in microcapsules A or B or in the free perfume oil (see Example 5).

In a first aspect, the present invention relates to a perfume system comprising:

a) a core-shell microcapsule A, b) optionally, a core-shell microcapsule B; and c) optionally, a free perfume oil, wherein the core of the core-shell microcapsule A and/or the free perfume oil, if present, comprises a 2-oxoacetate derivative of formula (I)

(I)

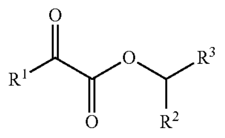

wherein $R^1$ represents a linear or branched $C_1$ to $C_{22}$ alkyl or alkenyl group, optionally containing one to four oxygen atoms that are not directly connected to the carbonyl group, or a cyclic $C_3$ to $C_8$ alkyl or alkenyl group, optionally containing one to four oxygen atoms that are not directly connected to the carbonyl group, or a phenyl group, optionally substituted with a $C_1$ to $C_4$ alkyl group, $R^2$ represents a linear, branched or cyclic $C_1$ to $C_{22}$ hydrocarbon group, optionally containing one to four oxygen atoms, and $R^3$ represents a hydrogen atom or a $C_1$ to $C_{10}$ hydrocarbon group, optionally containing one to two oxygen atoms;

or $R^2$ and $R^3$, when taken together, form a $C_{5-16}$ cycloalkyl, $C_{5-16}$ cycloalkenyl, $C_{4-14}$ heterocycloalkyl or $C_{4-14}$ heterocycloalkenyl group.

For the sake of clarity, by the expression "optionally", it is meant that the optional component may be comprised in the perfume system or not.

For the sake of clarity, by the expression "perfume system" it is meant that a perfuming composition is designed to provide an olfactive impression to the consumer by using a fragrance delivery system, such as a microcapsule or a core-shell microcapsule. In a particular embodiment, the perfume system is designed to provide a long-lasting and/or a high performance of the perfume to the consumer.

For the sake of clarity, by the expression "core-shell microcapsule" or the similar, it is meant to designate a capsule that has a particle size distribution in the micron range (e.g. a mean diameter (d(v, 0.5)) comprised between about 1 and 3000 μm) and comprises an external solid oligomer-based shell or a polymeric shell and an internal continuous phase being an oil phase (i.e. hydrophobic material) enclosed by the external shell. For avoidance of doubts coacervates are also considered as core-shell microcapsules in the present invention.

According to an embodiment, microcapsules have a mean diameter comprised between 1 and 500 microns, preferably from 2 and 200, more preferably between 4 and 100 microns.

Core-shell microcapsules A and B can be of the same shell type or of different shell types. The nature of the shell of the microcapsules can vary.

The material encapsulating the hydrophobic material composition can be microcapsules which have been widely described in the prior art.

According to a particular embodiment, the shell comprises a material selected from the group consisting of polyurea, polyurethane, polyamide, polyester, poly(meth) acrylate (i.e. polyacrylate and/or polymethacrylate), polysiloxane, polycarbonate, polysulfonamide, polymers of urea and formaldehyde, melamine and formaldehyde, melamine and urea, or melamine and glyoxal and mixtures thereof. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to a particular embodiment, the core-shell microcapsule(s) can be also derived by using different or more than one encapsulation method.

In a preferred embodiment, the shell of microcapsules A and B may be, each independently, selected from the group of aminoplast, polyamide, polyester, polyurea and polyurethane shells and mixtures thereof.

In a particular embodiment, the shell of microcapsules A and/or B comprises an aminoplast copolymer, such as melamine-formaldehyde or urea-formaldehyde or cross-linked melamine formaldehyde or melamine glyoxal.

In a particular embodiment, the shell of microcapsules A and/or B is polyurea-based made from, for example but not limited to isocyanate-based monomers and amine-containing crosslinkers such as guanidine carbonate and/or guanazole. Certain polyurea microcapsules comprise a polyurea wall which is the reaction product of the polymerisation between at least one polyisocyanate comprising at least two isocyanate functional groups and at least one reactant selected from the group consisting of an amine (for example a water-soluble guanidine salt and guanidine); a colloidal stabilizer or emulsifier; and an encapsulated perfume. However, the use of an amine can be omitted.

In a particular embodiment, the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). In a particular embodiment, the emulsifier is an anionic or amphiphilic biopolymer, which may be for example chosen from the group consisting of gum Arabic, soy protein, gelatin, sodium caseinate and mixtures thereof.

In a particular embodiment, the shell of microcapsules A and/or B is polyurethane-based made from, for example but not limited to polyisocyanate and polyols, polyamide, polyester, etc.

In a particular embodiment, the microcapsules A and/or B have a polymeric shell resulting from complex coacervation wherein the shell is possibly cross-linked.

In a particular embodiment of the core-shell microcapsules, the core-shell microcapsules A and/or B comprise an oil-based core comprising a hydrophobic active, preferably perfume, and a composite shell comprising a first material and a second material, wherein the first material and the second material are different, the first material is a coacervate, the second material is a polymeric material.

In a particular embodiment, the weight ratio between the first material and the second material is comprised between 50:50 and 99.9:0.1.

In a particular embodiment, the coacervate comprises a first polyelectrolyte, preferably selected among proteins (such as gelatin), polypeptides or polysaccharides (such as chitosan), most preferably Gelatin and a second polyelectrolyte, preferably alginate salts, cellulose derivatives guar gum, pectinate salts, carrageenan, polyacrylic and methacrylic acid or xanthan gum, or yet plant gums such as acacia gum (Gum Arabic), most preferably Gum Arabic.

The coacervate first material can be hardened chemically using a suitable cross-linker such as glutaraldehyde, glyoxal, formaldehyde, tannic acid or genipin or can be hardened enzymatically using an enzyme such as transglutaminase.

The second polymeric material can be selected from the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof, preferably polyurea and/or polyurethane. The second material is preferably present in an amount less than 3 wt-%, preferably less than 1 wt-% based on the total weight of the microcapsule slurry.

The preparation of an aqueous dispersion/slurry of core-shell microcapsules is well known by a skilled person in the art. In a particular embodiment, the microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Missouri U.S.A.), Cytec Industries (West Paterson, New Jersey U.S.A.), Sigma-Aldrich (St. Louis, Missouri U.S.A.).

In a particular embodiment of the core-shell microcapsules, the core-shell microcapsules A and/or B comprise

- an oil-based core comprising a hydrophobic active, preferably a perfume,
- optionally an inner shell made of a polymerized polyfunctional monomer;
- a biopolymer shell comprising a protein, wherein at least one protein is cross-linked.

According to a particular embodiment, the protein is chosen from the group consisting of milk proteins, caseinate salts such as sodium caseinate or calcium caseinate, casein, whey protein, hydrolyzed proteins, gelatins, gluten, pea protein, soy protein, silk protein and mixtures thereof, preferably sodium caseinate, most preferably sodium caseinate.

According to a particular embodiment, the protein comprises sodium caseinate and a globular protein, preferably chosen from the group consisting of whey protein, beta-lactoglobulin, ovalbumine, bovine serum albumin, vegetable proteins, and mixtures thereof.

The protein is preferably a mixture of sodium caseinate and whey protein.

According to a particular embodiment, the biopolymer shell comprises a crosslinked protein chosen from the group consisting of sodium caseinate and/or whey protein.

According to a particular embodiment, the core-shell microcapsules A and/or B comprise:

an oil-based core comprising the hydrophobic active, preferably a perfume;

an inner shell made of a polymerized polyfunctional monomer; preferably a polyisocyanate having at least two isocyanate functional groups;

a biopolymer shell comprising a protein, wherein at least one protein is cross-linked; wherein the protein contains preferably a mixture comprising sodium caseinate and a globular protein, preferably whey protein;

optionally at least an outer mineral layer.

According to an embodiment, sodium caseinate and/or whey protein is (are) cross-linked protein(s).

The weight ratio between sodium caseinate and whey protein is preferably comprised between 0.01 and 100, preferably between 0.1 and 10, more preferably between 0.2 and 5.

In a particular embodiment, the microcapsules A and/or B are one-shell aminoplast core-shell microcapsules obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) preparing an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain the dried core-shell microcapsule.

In a particular embodiment, the core-shell microcapsules A and/or B are formaldehyde-free capsules. A typical process for the preparation of aminoplast formaldehyde-free microcapsules slurry comprises the steps of 1) preparing an oligomeric composition comprising the reaction product of, or obtainable by reacting together:
   a. a polyamine component in the form of melamine or of a mixture of melamine and at least one $C_1$-$C_4$ compound comprising two $NH_2$ functional groups;
   b. an aldehyde component in the form of a mixture of glyoxal, a $C_{4-6}$ 2,2-dialkoxy-ethanal and optionally a glyoxalate, said mixture having a molar ratio glyoxal/$C_{4-8}$ 2,2-dialkoxy-ethanal comprised between 1/1 and 10/1; and
   c. a protic acid catalyst;
2) preparing an oil-in-water dispersion, wherein the droplet size is comprised between 1 and 600 microns, and comprising:
   a. an oil;
   b. a water medium:
   c. at least an oligomeric composition as obtained in step 1;
   d. at least a cross-linker selected amongst:
      i. $C_4$-$C_{12}$ aromatic or aliphatic di- or tri-isocyanates and their biurets, triurets, trimmers, trimethylol propane-adduct and mixtures thereof; and/or
      ii. a di- or tri-oxiran compounds of formula:

Q-(oxiran-2-ylmethyl)$_n$ wherein n stands for 2 or 3 and Q represents a $C_2$-$C_6$ group optionally comprising from 2 to 6 nitrogen and/or oxygen atoms;
   e. optionally a $C_1$-$C_4$ compounds comprising two $NH_2$ functional groups;
3) Heating the dispersion; and
4) Cooling the dispersion.

The above process is described in more details in WO 2013/068255.

In a particular embodiment, the core-shell microcapsules A and/or B comprise:

an oil based core comprising an hydrophobic active, preferably a perfume, and a polyamide shell comprising or being obtainable from:
   an acyl chloride,
   a first amino compound, and
   a second amino compound.

According to a particular embodiment, the core-shell microcapsules A and/or B comprise:

an oil based core comprising an hydrophobic active, preferably a perfume, and a polyamide shell comprising or being obtainable from:

an acyl chloride, preferably in an amount comprised between 5 and 98%, preferably between 20 and 98%, more preferably between 30 and 85% w/w a first amino compound, preferably in an amount comprised between 1% and 50% w/w, preferably between 7 and 40% w/w;

a second amino compound, preferably in an amount comprised between 1% and 50% w/w, preferably between 2 and 25% w/w a stabilizer, preferably a biopolymer, preferably in an amount comprised between 0 and 90%, preferably between 0.1 and 75%, more preferably between 1 and 70%.

According to a particular embodiment, the core-shell microcapsules A and/or B comprise:

an oil based core comprising a hydrophobic active, preferably a perfume, and a polyamide shell comprising or being obtainable from:
   an acyl chloride,
   a first amino-compound being an amino-acid, preferably chosen from the group consisting of L-Lysine, L-Arginine, L-Histidine, L-Tryptophane and/or mixture thereof.
   a second amino compound chosen from the group consisting of ethylene diamine, diethylene triamine, cystamine and/or a mixture thereof, and
   a biopolymer chosen from the group consisting of casein, sodium caseinate, bovin serum albumin, whey protein, and/or a mixture thereof;

wherein the first amino-compound can be different from the second amino-compound.

Typically, a process for preparing polyamide-based microcapsules A and/or B includes the following steps:

a) Dissolving at least one acyl chloride in a hydrophobic material, preferably a perfume to form an oil phase;
b) Dispersing the oil phase obtained in step a) into a water phase comprising a first amino compound to form an oil-in water emulsion;
c) Performing a curing step to form polyamide microcapsules in the form of a slurry;

wherein a stabilizer is added in the oil phase and/or in the water phase, and wherein at least a second amino-compound is added in the water phase before the formation of the oil-in-water emulsion and/or in the oil-in water emulsion obtained after step b).

In a particular embodiment, the shell of the microcapsule A and/or B is polyurea- or polyurethane-based. Examples of processes for the preparation of polyurea and polyurethane-based microcapsule slurry are for instance described in WO 2007/004166, EP 2300146, and EP 2579976. Typically a process for the preparation of polyurea or polyurethane-based microcapsule slurry include the following steps:

a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 μm, preferably between 5 and 50 μm; and
d) Applying conditions sufficient to induce interfacial polymerisation and form microcapsules in form of a slurry.

In a particular embodiment, the microcapsules A and/or B can be in form of a powder, which in particular may be obtained by submitting the microcapsule slurry to a drying step, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, gum Arabic, vegetable gums, pectins, xanthans, alginates, carrageenans or cellulose derivatives to provide microcapsules in a powder form.

However, one may cite also other drying methods such as extrusion, plating, spray granulation, the fluidized bed process, or even drying at room temperature using materials (carrier, desiccant) that meet specific criteria as disclosed in WO 2017/134179.

The core(s) of the core-shell microcapsule(s) A and/or B is/are in form of an oil phase. By the term "oilphase" of the core or "core oilphase" it is meant a liquid or a solution, at 20° C. and 1 atm of pressure, and which is capable of bringing a benefit or effect into its surrounding environment, and in particular comprises a perfuming, flavoring, cosmetic, skin caring, malodor counteracting, bactericide, fungicide, pharmaceutical or agrochemical ingredient, a diagnostic agent and/or an insect repellent or attractant.

Said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient, a diagnostic agent and/or as an insect repellent or attractant.

Preferably, said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient and/or as an insect repellent or attractant.

Practically, the invention is carried out exactly in the same manner, independently of the exact properties of the oil phase. Therefore, it is understood that, even if the invention will be further illustrated herein below with a specific reference to "perfuming" ingredients, the below embodiments are also applicable to other oils (i.e. it is possible to replace the expression "perfuming" with "flavoring", "cosmetic", "skin caring", "malodor counteracting", "bactericide", "fungicide", "pharmaceutical", "agrochemical", "diagnostic agent", "insect attractant" or with "insect repellent" for instance).

In a preferred embodiment, the oil phase comprises a perfume and, optionally, solvents, optionally, a perfume co-ingredient and, optionally, a perfume adjuvant.

By the term "perfume" it is understood a single perfuming ingredient or a mixture of ingredients in the form of a perfuming composition.

By the terms "perfuming ingredients" or "perfume co-ingredients" are understood here compounds which are used as active ingredients in perfuming preparations or compositions in order to impart a hedonic effect when applied to a surface. In other words, such compounds, to be considered as being perfuming ones, must be recognized by a person skilled in the art of perfumery as being able to impart or modify in a positive or pleasant way the odor of a composition or of an article or surface, and not just as having an odor. Moreover, this definition is also meant to include compounds that do not necessarily have an odor but are capable of modulating the odor of a perfuming composition, perfumed article or surface and, as a result, of modifying the perception by a user of the odor of such a composition, article or surface.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general, perfuming ingredients belong to chemical classes as varied as hydrocarbons, alcohols, lactones, aldehydes, ketones, esters, ethers, acetates, nitriles, thiols, terpenoids, nitrogenous or sulphurous heterocyclic compounds and essential oils, and said perfuming ingredients can be of natural or synthetic origin. Specific examples of such perfuming ingredients can be found in the current literature, for example in Perfume and Flavour Chemicals, by S. Arctander, Montclair N.J. (USA), 1969 (and later editions), or in other works of a similar nature, as well as in the vast patent and other literature related to the perfume industry. They are well known to the person skilled in the art of perfuming consumer products, that is, of imparting a pleasant odour to a consumer product.

By "solvent" it is meant a material which is practically neutral from a perfumery point of view, i.e. that does not significantly alter the organoleptic properties of perfuming ingredients and is generally not miscible with water, i.e. possesses a solubility in water below 10%, or even below 5%. Solvents commonly used in perfumery, such as for example dipropyleneglycol, diethyl phthalate, isopropyl myristate, benzyl benzoate, 2-(2-ethoxyethoxy)-1-ethanol or ethyl citrate, limonene or other terpenes, isoparaffins such as those known under the trademark Isopar® (origin: Exxon Chemical) or glycol ethers and glycol ether esters such as those known under the trademark Dowanol® (origin: Dow Chemical Company), are suitable solvents for the purposes of the invention.

By "perfumery adjuvant" it is meant an ingredient capable of imparting additional added benefits such as a color, chemical stability, etc. A detailed description of the nature and type of adjuvant commonly used in perfuming bases cannot be exhaustive, but it has to be mentioned that said ingredients are well known to a person skilled in the art.

The 2-oxoacetate derivative of formula (I) can be used inside the core-shell microcapsules e.g. as part of the oil phase, in particular inside the core-shell microcapsule A, to generate a gas upon exposure to light and thus to expand or break the capsule wall. Furthermore, 2-oxoacetates of formula (I) can be used as profragrances inside the core-shell microcapsules and/or in the free perfume to generate, upon exposure to light, a perfuming aldehyde or ketone in addition to the gas.

Preferably, $R^1$ represents a linear or branched $C_1$ to $C_4$ alkyl or alkenyl group, or a cyclic $C_3$ to $C_7$ alkyl or alkenyl group, or a phenyl group, optionally substituted with a $C_1$ to $C_4$ alkyl group. More preferably, $R^1$ represents a methyl group, a cyclopentyl, a cyclohexyl or a phenyl group. Most preferably, $R^1$ represents a phenyl group.

Preferably, $R^2$ represents a linear, branched or cyclic $C_4$ to $C_{20}$ hydrocarbon group, optionally containing one to four oxygen atoms.

Preferably, $R^3$ represents either a hydrogen atom or a $C_1$ to $C_{10}$ hydrocarbon group, optionally containing one to two oxygen atoms.

Preferably, $R^2$ and $R^3$, when taken together, form a $C_{5-16}$ cycloalkyl, $C_{5-16}$ cycloalkenyl, $C_{4-14}$ heterocycloalkyl or $C_{4-14}$ heterocycloalkenyl group.

More preferably the $OCH(R^2)(R^3)$ group in formula (I) is derived from the corresponding $C_6$ to $C_{20}$ perfumery aldehyde of formula $O{=}CH(R^2)$ (i.e. $R^3$ is H) or the corresponding $C_6$ to $C_{20}$ perfumery ketone of formula $O{=}C(R_2)(R_3)$.

Even more preferably, the $OCH(R^2)(R^3)$ group in formula (I) is derived from the corresponding $C_6$ to $C_{12}$ perfumery aldehyde of formula $O{=}CH(R^2)$.

Most preferably the perfumery aldehyde of formula $O{=}CH(R^2)$ is selected from the group consisting of benzaldehyde, 2,4-dimethyl-3-cyclohexene-1-carbaldehyde, 2,6-dimethyl-5-heptenal (melonal), 3,7-dimethyl-2,6-octadienal (citral), 3,7-dimethyl-6-octenal (citronellal), decanal, 4-dodecenal, 3-hexenal, 7-hydroxy-3,7-dimethyloctanal, 2-methylundecanal and 2-phenylacetaldehyde.

Most preferably the perfumery ketone of formula $O{=}C(R^2)(R^3)$ is selected from the group consisting of oct-2-en-4-one and 2-isopropyl-5-methylcyclohexan-1-one.

In a particular embodiment, the 2-oxoacetate derivative of formula (I) is selected from the group consisting of 3-(4-tert-butyl-1-cyclohexen-1-yl)propyl 2-oxo-2-phenylacetate, 3-(4-tert-butylphenyl)-2-methylpropyl 2-cyclohexyl-2-oxoacetate, 3-(4-(tert-butyl)phenyl)-2-methylpropyl 2-oxo-2-phenylacetate, decyl 2-cyclohexyl-2-oxoacetate, decyl 2-oxo-2-phenylacetate, (2,4-dimethyl-3-cyclohexen-1-yl) methyl 2-cyclohexyl-2-oxoacetate, (2,4-dimethyl-3-cyclohexen-1-yl)methyl 2-oxo-2-phenylacetate, 1-(3,3- and 5,5-dimethyl-1-cyclohexen-1-yl)-4-pentenyl 2-oxo2-phenylacetate, 3-(3,3- and 1,1-dimethyl-2,3-dihydro-1H-inden-5-yl)propyl 2-oxo-2-phenylacetate, 2,6-dimethyl-5-heptenyl 2-oxo-2-phenylacetate, 3,7-dimethyl-2,6-octadienyl 2-cyclohexyl-2-oxoacetate, 3,7-dimethyl-2,6-octadienyl 2-(4-methylcyclohexyl)-2-oxoacetate, 3,7-dimethyl-2,6-octadienyl 3-methyl-2-oxopentanoate, 3,7-dimethyl-2,6-octadienyl 2-oxo-2-phenylacetate, 3,7-dimethyl-2,6-octadienyl 2-oxopropanoate, 3,7-dimethyl-6-octenyl 2-(4-acetylphenyl)-2-oxoacetate, 3,7-dimethyl-6-octenyl (bicyclo[2.2.1]hept-2exo-yl)oxoacetate, 3,7-dimethyl-6-octenyl 2-cyclohexyl-2-oxoacetate, 3,7-dimethyl-6-octenyl 2-cyclopentyl-2-oxoacetate, 3,7-dimethyl-6-octenyl 2-(4-methylcyclohexyl)-2-oxoacetate, 3,7-dimethyl-6-octenyl[4-(2-methyl-1,3-dioxolan-2-yl)phenyl]oxoacetate, 3,7-dimethyl-6-octenyl 3-methyl-2-oxopentadecanoate, 3,7-dimethyl-6-octenyl 3-methyl-2-oxopentanoate, 3,7-dimethyl-6-octenyl 2-oxobutanoate, 3,7-dimethyl-6-octenyl 2-oxohexadecanoate, 3,7-dimethyl-6-octenyl 2-oxopentanoate, 3,7-dimethyl-6-octenyl 2-oxo-2-phenylacetate, 3,7-dimethyl-6-octenyl 2-oxopropanoate, 4-(1,1-dimethylpropyl)cyclohexyl 2-cyclohexyl-2-oxoacetate, 4-dodecenyl 2-oxo-2-phenylacetate, (3,5,5,6,7,8,8-heptamethyl-5,6,7,8-tetrahydronaphthalen-2-yl)methyl 2-oxo-2-phenylacetate, 1-(3,5,5,6,8,8-hexamethyl-5,6,7,8-tetrahydro-2-naphthalenyl)ethyl 2-oxo-2-phenylacetate, 3-hexenyl 2-oxo-2-phenylacetate, 3-hexenyl 2-oxopropanoate, 7-hydroxy-3,7-dimethyloctyl 2-oxo2-phenylacetate, [4- and 3-(4-hydroxy-4-methylpentyl)-3-cyclohexen-1-yl] methyl 2-oxo-2-phenylacetate, 2-isopropyl-5-methylcyclohexyl 2-cyclohexyl-2-oxoacetate, 2-isopropyl-5-methylcyclohexyl 2-oxo-2-phenylacetate, 4-methoxybenzyl 2-cyclohexyl-2-oxoacetate, [4- and 3-(4-methyl-3-pentenyl)-3-cyclohexen-1-yl]methyl 2-oxo-2-phenylacetate, 3-methyl-5-phenylpentyl 2-oxo-2-phenylacetate, 2-methyl-4-(2',2',3'-trimethyl-3'-cyclopenten-1'-yl)-4-pentenyl 2-oxo-2-phenylacetate, 2,6-nonadienyl 2-oxo-2-phenylacetate, 3-nonenyl 2-oxo-2-phenylacetate, oct-2-en-4-yl 2-oxo-2-phenylacetate, 2-pentylcyclopentyl 2-cyclohexyl-2-oxoacetate, 4-phenylbutan-2-yl 2-oxo-2-phenylacetate, 2-phenylethyl 2-oxo-2-phenylacetate, 2-phenylethyl 2-oxopropanoate, 3,5,6,6-tetramethyl-4-methyleneheptan-2-yl 2-oxo-2-phenylacetate, 4-(2,6,6-trimethyl-2-cyclohexenyl)-3-buten-2-yl 2-oxo-2-phenylacetate, benzyl 2-oxo-2-phenylacetate, 2-hexenyl 2-oxo-2-phenylacetate, 2-methylundecyl 2-oxo-2-phenylacetate, 9-undecenyl 2-oxo-2-phenylacetate or 10-undecenyl 2-oxo-2-phenylacetate. Particularly, the 2-oxoacetate derivative of formula (I) may be 2-phenylethyl 2-oxo-2-phenylacetate, 3-hexenyl 2-oxo-2-phenylacetate, benzyl 2-oxo-2-phenylacetate, (2,4-dimethyl-3-cyclohexen-1-yl)methyl 2-oxo-2-phenylacetate, 3,7-dimethyl-2,6-octadienyl 2-oxo-2-phenylacetate, 3,7-dimethyl-6-octenyl 2-oxo-2-phenylacetate, 7-hydroxy-3,7-dimethyloctyl 2-oxo-2-phenylacetate, decyl 2-oxo-2-phenylacetate, 4-dodecenyl 2-oxo-2-phenylacetate, 2-isopropyl-5-methylcyclohexyl 2-oxo-2-phenylacetate, 2-methylundecyl 2-oxo-2-phenylacetate, oct-2-en-4-yl 2-oxo-2-phenylacetate or 2,6-dimethyl-5-heptenyl 2-oxo-2-phenylacetate.

It is understood that by "hydrocarbon group" it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynil group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

For the sake of clarity, by the expression "optionally comprising . . . ", "optionally containing . . . " or "optionally substituted . . . " or similar, it is meant that that the group, to which is made reference, may comprise, contain or may be substituted with e.g. the following functional group or groups: alcohol, ketone, aldehyde, ether, ester and/or carboxylic acid group.

2-Oxoacetate derivatives of formula (I) are encapsulated in core-shell microcapsules A or used in the free perfume oil or in a combination thereof. According to the present invention, the 2-oxoacetate derivative of formula (I) in the core-shell microcapsule A and/or in the free perfume oil can be one single structure according to formula (I) or a mixture of different structures according to formula (I).

In a particular embodiment, the perfume system comprises the core-shell microcapsule A and a free perfume oil. In another particular embodiment, the perfume system comprises the core-shell microcapsule A and a core-shell microcapsule B.

In a particular embodiment, the perfume system comprises the core-shell microcapsule A, the core-shell microcapsule B and the free perfume oil.

The perfume system according to the present invention comprises a core-shell microcapsule A.

In a particular embodiment, the core-shell microcapsule A of the perfume system comprises

- at least one 2-oxoacetate derivative of formula (I),
- optionally, at least one perfumery raw material of Group A,
- at most 20 wt-% of a perfumery raw material of Group B and
- optionally, a solvent.

In a preferred embodiment, core-shell microcapsule A comprises at least one 2-oxoacetate derivative of formula (I).

The core-shell microcapsules A thus preferably comprises at least one 2-oxoacetate of formula (I) and, optionally, one or several perfumery raw materials of Group A, at most 20 wt-% of one or several perfumery raw material of Group B and, optionally, a solvent.

Preferably, the amount of the 2-oxoacetate derivative of formula (I) in the core-shell microcapsule A is at least 25 wt-%, more preferably at least 50 wt-%, more preferably at least 80 wt-% and most preferably at least 90 wt-% (based on the total mass of the microcapsule A).

Core-shell microcapsules A, that contain almost exclusively one or several 2-oxoacetate derivatives of formula (I) have the particular advantage to more easily generate a gas overpressure inside the capsule and thus expand or cleave the capsule wall more easily to release the photochemically generated perfume raw material.

In case a perfume is encapsulated, it is preferred that the 2-oxoacetate derivative of formula (I) is in a separate capsule.

Perfumery raw materials of Group A are not (or only to a minimum extent) interfering with the light-induced degradation of the 2-oxoacetate derivative of formula (I). Perfumery raw materials of Group A can be used in the perfume system according to the invention in quantities that are independent of the amount of 2-oxoacetate derivative of formula (I).

By the term "interfering with the light-induced degradation of the 2-oxoacetate" it is meant that the presence of these raw materials has a negative impact on the rate of the light-induced degradations of the 2-oxoacetates as compared to their absence. This means that the presence of these compounds slows the degradation of the 2-oxoacetates or even prevents it. There are several ways how perfumery raw materials might interfere with the degradation of 2-oxoacetates, such as for example by strongly absorbing UVA radiation or by quenching any of the intermediate (excited) states of the photoreaction.

Perfumery raw materials are considered as being of Group A if 50% or less of ethyl 2-oxo-2-phenylacetate (used as a reference compound) are remaining after irradiation of the perfumery raw material and the 2-oxoacetate (at 1.5 g $L^{-1}$) in a weight ratio of 1:1 in non-degassed acetonitrile with UVA radiation at 3.1 mW $cm^{-2}$ for 40 min at 25° C.

The perfumery raw material of Group A of the perfume system of the present invention is selected from the group consisting of allyl 2-(cyclohexyloxy)acetate, allyl 3-cyclohexylpropanoate, allyl heptanoate, allyl hexanoate, benzaldehyde, benzyl acetate, benzyl benzoate, benzyl 2-hydroxybenzoate, 2-cyclohexylethyl acetate, cyclohexyl 2-hydroxybenzoate, 4-cyclohexyl-2-methyl-2-butanol, decanal, diethyl 1,4-cyclohexanedicarboxylate, (2,2-dimethoxyethyl)benzene, 6,6-dimethoxy-2,5,5-trimethyl-2-hexene, 2-(6,6-dimethylbicyclo[3.1.1]hept-2-en-2-yl)ethyl acetate, 2,4-dimethyl-3-cyclohexene-1-carbaldehyde, 1-(5,5-dimethyl-1-cyclohexen-1-yl)-4-penten-1-one, 2,6-dimethyl-2-heptanol, 2,6-dimethyl-5-heptenal, 6,6-dimethyl-2-methylenebicyclo[3.1.1]heptane, 3,7-dimethyl-2,6- and 3,6-nonadienenitrile, 3,7-dimethyl-1,6-nonadien-3-ol, 3,7-dimethyl-2,6-octadienal, (E)-3,7-dimethyl-2,6-octadienol, (Z)-3,7-dimethyl-2,6-octadienol, 3,7-dimethyl-1,6-octadien-3-ol, 3,7-dimethyl-2,6-octadienyl acetate, 3,7-dimethyl-3-octanol, 3,7-dimethyl-6-octenenitrile, 3,7-dimethyl-6-octen-1-ol, 2,6-dimethyl-7-octen-2-ol, 3,7-dimethyl-6-octenyl acetate, 1,1-dimethyl-2-phenylethyl butanoate, 1,1-dimethyl-2-phenylethyl acetate, 3,3-dimethyl-5-[2,2,3-trimethyl-3-cyclopenten-1-yl]-4-penten-2-ol, 1,4-dioxacycloheptadecane-5,17-dione, dodecanal, dodecanol, (Z)-4-dodecenal, ethyl butanoate, ethyl 3-hydroxybut-2-enoate, ethyl 2-methylbutanoate, ethyl 2-methyl-1,3-dioxolane-2-acetate, ethyl 2-methylpentanoate, ethyl 3-oxobutanoate, 3-(2- and 4-ethylphenyl)-2,2-dimethylpropanal, (2E)-2-ethyl-4-[2,2,3-trimethyl-3-cyclopenten-1-yl]-2-buten-1-ol, 6-ethyl-2,10,10-trimethyl-1-oxaspiro[4.5]deca-3,6-diene, 5-heptyldihydro-2(3H)-furanone, 4,6,6,7,8,8-hexamethyl-1,3,4,6,7,8-hexahydrocyclopenta[g]isochromene, 1-(3,5,5,6,8,8-hexamethyl-5,6,7,8-tetrahydro-2-naphthalenyl)ethanone, (Z)-3-hexen-1-ol, (Z)-3-hexenyl acetate, (Z)-3-hexenyl 2-hydroxybenzoate, hexyl acetate, 5-hexyldihydrofuran-2(3H)-one, hexyl 2-hydroxybenzoate, hexyl 2-methylpropanoate, 3- and 4-(4-hydroxy-4-methylpentyl)-3-cyclohexene-1-carbaldehyde, 1-isopropyl-4-methylbenzene, 2-isopropyl-5-methylcyclohexan-1-ol, isopropyl 2-methylbutanoate, 4-isopropyl-1-methylcyclohexyl acetate, 3-(3-isopropyl-1-phenyl)butanal, 3-(4-isopropylphenyl)-2-methylpropanal, isopropyl tetradecanoate, 4-methoxybenzaldehyde, 1-methoxy-4-methylbenzene, 3-(4-methoxyphenyl)-2-methylpropanal, 4-(2-methoxy-2-propanyl)-1-methylcyclohexene, 1-methoxy-4-(2-propenyl)benzene, 6-methoxy-3,6,8,8-tetramethyloctahydro-1H-3a,7-methanoazulene, methyl benzoate, 7-methyl-2H-1,5-benzodioxepin-3(4H)-one, 3-methyl-2-buten-1-yl acetate, 2- and 3-methylbutyl acetate, 2- and 3-methylbutyl butyrate, 2-methylbutyl 2-hydroxybenzoate, 2-(4-methylcyclohex-3-enyl)propan-2-ol, 2-(4-methyl-3-cyclohexen-1-yl)-2-propanyl acetate, 2-{2-[4-methyl-3-cyclohexen-1-yl]propyl}cyclopentanone, (E)-4-methyl-3-decen-5-ol, methyl 2,2-dimethyl-6-methylidenecyclohexanecarboxylate, methyl 2,4-dihydroxy-3,6-dimethylbenzoate, 5-methylheptan-3-one oxime, methyl 7-isopropyl-1,4a-dimethyl-1,2,3,4,4a,4b,5,6,7,8,10,10a-dodecahydrophenanthrene-1-carboxylate and methyl 7-isopropyl-1,4a-dimethyltetradecahydrophenanthrene-1-carboxylate, 1-methyl-4-(4-methyl-3-pentenyl)-3-cyclohexene-1-carbaldehyde, 2-methyl-3-[4-(2-methyl-2-propanyl)phenyl]propanal, 4-methyl-2-(2-methyl-1-propen-1-yl)tetrahydro-2H-pyran, methyl 2-octynoate, methyl 2-(3-oxo-2-pentylcyclopentyl)acetate, 4-methyl-4-penten-2-yl 2-methylpropanoate, 3-methyl-5-phenyl-1-pentanol, 5-methyl-2-(2-propanyl)cyclohexanone, 1-methyl-4-(2-propanyl)-1,4-cyclohexadiene, 4-(2-methyl-2-propanyl)cyclohexanol, 2-(2-methyl-2-propanyl)cyclohexyl acetate, 4-(2-methyl-2-propanyl)cyclohexyl acetate, 1-methyl-4-(prop-1-en-2-yl)cyclohex-1-ene, 2-methyl-4-propyl-1,3-oxathiane, (3E)-3-methyl-4-(2,6,6-trimethyl-2-cyclohexan-1-yl)-3-buten-2-one, methyl 2,6,6-trimethyl-3-cyclohexene-1-carboxylate, (3E)-3-methyl-4-(2,6,6-trimethyl-2-cyclohexen-1-yl)-3-buten-2-one and (1E)-1-(2,6,6-trimethyl-2-cyclohexen-1-yl)-1-penten-3-one, 3-methyl-5-(2,2,3-trimethyl-3-cyclopenten-1-yl)-2-pentanol, 2-methylundecanal, 2,6-nonadienal, 2,6-nonadienol, nonanal, octanal, oct-2-en-4-one, oxacyclohexadecan-2-one, 1-oxa-12- and 13-cyclohexadecen-2-one, 1,1'-oxydibenzene, pentyl 2-hydroxybenzoate, 2-phenoxyethanol, 2-phenylacetaldehyde, 3-phenylbutanal, 2-phenylethanol, 2-phenylethyl acetate, phenylmethanol, 4-[(2-propanyl)cyclohexyl]methanol, 7-propyl-2H-benzo[b][1,4]dioxepin-3(4H)-one, tetrahydro-2-isobutyl-4-methyl-4(2H)-pyranol, 3a,6,6,9a-tetramethyldodecahydronaphtho[2,1-b]furan, 1-(3,6,8,8-tetramethyl-2,3,4,7,8,8a-hexahydro-1H-3a,7-methanoazulen-5-yl)ethan-1-one, 2,3,6,7- and 2,4,6,8-tetramethylnonan-1-ol, 3,6,8,8-tetramethyloctahydro-1H-3a,7-methanoazulen-6-yl acetate, 2,2,6,8-tetramethyl-1,2,3,4,4a,5,8,8a-octahydro-1-naphthalenol, 1-(2,3,8,8-tetramethyl-1,2,3,4,5,6,7,8-, 1,2,3,5,6,7,8,8a- and 1,2,3,4,6,7,8,8a-octahydronaphthalen-2-yl)ethan-1-one, tricyclo[5.2.1.0(2,6)]dec-3- and 4-en-8-yl acetate, 2,2,2-trichloro-1-phenylethyl acetate, tricyclo[5.2.1.0(2,6)]dec-3- or 4-en-8-yl propanoate, 1,7,7-trimethylbicyclo[2.2.1]heptan-2-ol, 1,7,7-trimethylbicyclo[2.2.1]heptan-2-one, 1,7,7-trimethylbicyclo[2.2.1]heptan-2-yl acetate, 2,6,6-trimethylbicyclo[3.1.1]hept-2-ene, 2-(1,7,7-trimetylbicyclo[2.2.1]hept-2-yl)-1-cyclohexanol, 2-, 3- and 4-(5,5,6-trimethylbicyclo[2.2.1]hept-2-yl)-1-cyclohexanol, (2E)-1-[2,6,6-trimethyl-1-cyclohexen-1-yl]-2-buten-1-one, (2E)-1-(2,6,6-trimethyl-2-cyclohexen-1-yl)-2-buten-1-one, (2E)-1-(2,6,6-trimethyl-3-cyclohexen-1-yl)-2-buten-1-one, 3,8,9-, 4,6,8- and 4,7,9-trimethyldecan-2-ol, 1,3,3-trimethyl-2-oxabicyclo[2.2.2]octane, 2,2,5-trimethyl-5-pentylcyclopentanone, 2,6,6-trimethylspiro[bicyclo[3.1.1]heptane-3,1'-cyclohexane]-2'-en-4'-one, undecanal, 1,3,5-undecatriene and 10-undecenal.

The amount of perfumery raw materials of Group A in the core-shell microcapsule A may be present in amounts of more than 30 wt-%, more than 50 wt-%, more than 70 wt-% or more than 90 wt-% (based on the total mass of the microcapsule A). Particularly, the amount of perfumery raw materials of Group A in the core-shell microcapsule A may be present in amounts of at most 70 wt-%, preferably, of at most 60 wt-%, preferably, of at most 50 wt-%, preferably, of at most 40 wt-%, preferably, of at most 30 wt-%, preferably, of at most 20 wt-%, preferably, of at most 10 wt-%, more preferably, of at most 50 wt-%.

Perfumery raw materials of Group B are interfering with the light-induced degradation of the 2-oxoacetate derivative of formula (I). Such materials interact with the 2-oxoacetate derivative of formula (I) for example to slow the photoreaction which causes a reduced performance. Surprisingly, perfumery raw materials of Group B can still interfere with the light-induced degradation of 2-oxoacetates even if they are physically separated from the 2-oxoacetate, e.g. by encapsulating them into a separate capsule (microcapsule B) or by having them in the free perfume oil, while the 2-oxoacetate is e.g. encapsulated in microcapsule A. Perfumery raw materials of Group B should only be encapsulated to a minimum amount in core-shell microcapsules A or B, independent of whether the 2-oxoacetate is encapsulated in the same or in different core-shell microcapsules, or whether the 2-oxoacetate is part of the free perfume oil. Furthermore, perfume raw materials of Group B should also be used to a minimum amount in the free perfume oil, independent of whether the 2-oxoacetate is encapsulated or part of the free oil.

Perfumery raw materials are considered as being of Group B if more than 50% of ethyl 2-oxo-2-phenylacetate (used as a reference compound) are remaining after irradiation of the perfumery raw material and the 2-oxoacetate (at 1.5 g $L^{-1}$) in a weight ratio of 1:1 in non-degassed acetonitrile with UVA radiation at 3.1 mW $cm^{-2}$ for 40 min at 25° C.

The perfumery raw material of Group B of the perfume system of the present invention is selected from the group consisting of benzo[d][1,3]dioxole-5-carbaldehyde, (E)-1-(benzyloxy)-2-methoxy-4-(prop-1-en-1-yl)benzene, 2H-chromen-2-one, 1,2-dimethoxy-4-[(1E)-1-propen-1-yl]benzene, 1,5-dimethyl-1-vinyl-4-hexenyl (E)-3-phenylpropenoate, (E)-2-hexyl-3-phenyl-2-propenal, 4-(4-hydroxy-3-methoxyphenyl)-2-butanone, 2-isobutylquinoline, 2-methoxynaphthalene, 2-methoxy-4-(2-propen-1-yl)phenol, 2-methoxy-4-[(1E)-1-propen-1-yl]phenol, 2-methoxy-4-propylphenol, methyl 2-aminobenzoate, methyl N-[3-(4-tert-butylphenyl)-2-methyl-1-propenyl]anthranilate, methyl 2-(methylamino)benzoate, 6-methyl-1,2,3,4-tetrahydroquinoline, 1-(naphthalen-2-yl)ethan-1-one, (E)-2-pentyl-3-phenyl-2-propenal, (Z)-2-phenyl-2-hexenenitrile, (E)-3-phenyl-2-propen-1-ol, (2E)-1-(2,6,6-trimethyl-1,3-cyclohexadien-1-yl)-2-buten-1-one and (3E)-4-(2,6,6-trimethyl-1-cyclohexen-1-yl)-3-buten-2-one.

If perfumery raw materials of Group B are encapsulated, they will be retained more efficiently and thus prevent the photoreaction to occur for a longer and are therefore most preferably avoided or used in minimal amounts.

Therefore, the core-shell microcapsule A of the perfume system comprises at most 10 wt-% of a perfumery raw material of Group B; more preferably at most 5 wt-% of a perfumery raw material of Group B (based on the total mass of the microcapsule A) and most preferably, the core-shell microcapsule A of the perfume system does not contain a perfumery raw material of Group B.

The perfume system according to the present invention may further comprises an optional core-shell microcapsule B.

In a particular embodiment, the core-shell microcapsule B of the perfume system comprises at least one perfumery raw material of Group A, at most 30 wt-% of perfumery raw materials of Group B and optionally, a solvent.

The amount of perfumery raw materials of Group A in the core-shell microcapsule B is preferably at least 70 wt-%, more preferably at least 80 wt-%, and most preferably at least 90 wt-% (based on the total mass of microcapsule B).

The amount of perfumery raw materials of Group B is preferably below 30 wt-%, more preferably below 20 wt-%, even more preferably below 10 wt-% (based on the total mass of microcapsule B) and most preferably, the core-shell microcapsule B does not contain perfumery raw materials of Group B.

The perfume system according to the present invention further comprises an optionally free perfume oil. For the sake of clarity, by "free perfume oil" it is meant a perfume oil, e.g. as defined above, which is not encapsulated or part of the core-shell microcapsules A or B.

In a particular embodiment, the free perfume oil of the perfume system comprises at least one perfumery raw material of Group A, optionally, at least one perfumery raw material of Group B, optionally, at least one 2-oxoacetate derivative of formula (I) and, optionally, a solvent.

The amount of perfumery raw materials of Group A in the free perfume is preferably at least 70 wt-%, more preferably at least 80 wt-%, and most preferably at least 90 wt-% (based on the total mass of the free perfume).

Preferably, the free perfume oil comprises not more than 50 wt-% of perfumery raw materials of Group B, preferably below 30 wt-%, more preferably below 20 wt-%, even more preferably below 10 wt-% (based on the total mass of the free perfume).

Most preferably, the free perfume oil does not contain perfumery raw materials of Group B.

In a particular embodiment, the free perfume oil of the perfume system contains from 0.1 to 20 wt-% of the 2-oxoacetate derivative of formula (I). More preferably, the free perfume oil of the perfume system contains from 1 and 10 wt-% of the 2-oxoacetate derivative of formula (I), and most preferably between 2 and 5 wt-% of the 2-oxoacetate derivative of formula (I).

In a particular embodiment, the free perfume oil of the perfume system comprises a 2-oxoacetate derivative of formula (I) and the core-shell microcapsule A and the optionally core-shell microcapsule B does not comprise perfumery raw materials of Group B.

In a particular embodiment, the core-shell microcapsule A and the core-shell microcapsule B of the perfume system do not comprise perfumery raw materials of Group B.

More preferably, when the optionally free perfume oil does also not comprise perfumery raw materials of Group B, the core-shell microcapsule A comprises then a 2-oxoacetate derivative of formula (I) and the core-shell microcapsule B comprises at least one perfumery material of Group A.

Preferably, perfumery raw materials of Group B are part of the free perfume oil. Most preferably perfumery raw materials of Group B are not used in the presence of a 2-oxoacetate of formula (I).

In a particular embodiment, the perfume system comprises:

a. a core shell microcapsule A, wherein the core of the core-shell microcapsule A comprises, preferably consists of, a 2-oxoacetate derivative of formula (I) and optionally a solvent;

b. a core shell-microcapsule B, wherein the core of the core-shell microcapsule B comprises a perfume raw material of Group A; and c. optionally, a free perfume oil comprising at most 20% of a perfume raw material of Group B, or even no a perfume raw material of Group B, and/or a 2-oxoacetate derivative of formula (I) and/or a perfume raw material of Group A.

In a further aspect, the present invention relates to a perfuming composition comprising i) the perfume system, as defined above;

ii) at least one ingredient selected from the group consisting of a perfumery carrier and a perfumery base; and iii) optionally at least one perfumery adjuvant.

The term "perfumery carrier" is understood as a material which is practically neutral from a perfumery point of view i.e. that does not significantly alter the organoleptic properties of perfuming ingredients. In some embodiments, the carrier may be a liquid.

As liquid carriers one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as ethanol, water, dipropyleneglycol, diethyl phthalate, isopropyl myristate, benzyl benzoate, 2-(2-ethoxyethoxy)-1-ethanol or ethyl citrate, which are the most commonly used.

The term "perfumery base" is understood as a composition comprising at least one perfuming co-ingredient.

The term "perfuming co-ingredient" has the same meaning as defined above

The term "perfumery adjuvant" has the same meaning as defined above.

An invention's composition consisting of the invention's perfume system and at least one perfumery carrier represents a particular embodiment of the invention as well as a perfuming composition consisting of the invention's perfume system, at least one perfumery carrier, at least one perfumery base, and optionally at least one perfumery adjuvant.

In a further aspect, the present invention relates to a consumer product which comprises:

i) as perfuming ingredient, at least a perfume system, as defined above; and ii) a consumer product base.

Such consumer product may be a solid or a liquid product. According to a particular embodiment, liquid products are preferred. For the sake of clarity, by "consumer product" it is meant a consumer product which is typically perfumed and which is expected to deliver at least a perfuming effect, in other words it is a perfumed consumer product.

For the sake of clarity, by "consumer product base" we mean here a base formulation that is compatible with perfuming ingredients, and in particular with the perfume microcapsules according to the invention, comprising the photolabile 2-oxoacetate of formula (I), and is expected to deliver a pleasant odor to a surface to which it is applied (e.g. skin, hair, textile, or hard surface). In other words, a perfumed consumer product according to the invention comprises the unperfumed base functional formulation, corresponding to the desired consumer product, e.g. a detergent, a fabric softener, or an air freshener, for example, and an olfactive effective amount of the microcapsules according to the present invention. It goes without saying that such a consumer product may also contain non-encapsulated perfume, i.e. perfume ingredients in free form.

The nature and type of the constituents of the consumer product base do not warrant a more detailed description here, which in any case would not be exhaustive, the skilled person being able to select them on the basis of his general knowledge and according to the nature and the desired effect of said product.

In a particular embodiment, the perfumed consumer product comprises a perfume, a fabric care product, a body-care product, an air care product or a home care product.

In a particular embodiment, the perfumed consumer product is a fine perfume, a liquid or solid fabric detergent, a fabric softener, a fabric refresher, an ironing water, a shampoo, a coloring preparation, a hair spray, a deodorant or antiperspirant, a perfumed soap, shower or bath mousse, oil or gel, a hygiene product, an air freshener, a "ready to use" powdered air freshener or a hard-surface detergent. Most preferably, the perfumed consumer product is a liquid or solid fabric detergent, a fabric softener, a fabric refresher, an ironing water, an air freshener, a "ready to use" powdered air freshener or a hard-surface detergent. The proportions in which the perfume system according to the invention can be incorporated into the various aforementioned consumer products vary within a wide range of values. These values are dependent on the nature of the article to be perfumed and on the desired organoleptic effect as well as the nature of the co-ingredients in a given consumer product base. Typically, the consumer products comprise, based on the total consumer product mass, from about 0.01% to about 80% by weight, of the perfume system according to the present invention.

Preferably the consumer products comprise from about 0.01% to about 30% of the perfume system. More preferably the consumer products comprise from about 0.1% to about 15% of the perfume system.

In a further aspect, the present invention relates to a use of the perfumery system for enhancing, conferring, increasing and/or modifying the fragrance properties and/or the fragrance intensity of perfumed consumer products.

The definitions of the perfumery system and consumer products are the same as mentioned hereinabove.

The present invention also relates to a method for enhancing, conferring, increasing and/or modifying the fragrance properties and/or the fragrance intensity by applying a perfumery system as defined herein-above to a perfumed consumer product.

The definitions of the perfumery system and consumer products are the same as defined hereinabove.

In a further aspect, the present invention relates to a use of the perfumery system for intensifying or prolonging the diffusion effect of the characteristic fragrance of a perfume ingredient on a surface, characterized in that said surface is, preferentially in the presence in light, treat with the perfume system as defined herein-above or with a perfumed consumer product has defined herein-above under conditions which are susceptible of allowing the release of at least the aldehyde and/or ketone corresponding to the pertinent 2-oxoacetate of formula (I).

Suitable surfaces for such treatment are in particular textiles, hard surfaces, hair and skin.

The definitions of the perfumery system and consumer products are the same as defined herein-above.

The present invention also relates to a method for intensifying or prolonging the diffusion effect of the characteristic fragrance of a perfume ingredient on a surface, characterized in that said surface is, preferentially in the presence of light, treated with perfume system as defined herein-above or with a perfumed consumer product has defined herein-above under conditions which are susceptible of allowing the release of at least the aldehyde and/or ketone corresponding to the pertinent pro-fragrance (I).

Suitable surfaces for such treatment are in particular textiles, hard surfaces, hair and skin. Preferred surfaces for such treatment are textiles and hard surfaces.

The definitions of the perfumery system and consumer products are the same as defined herein-above.

EXAMPLES

The invention is hereafter described in a more detailed manner by way of the following examples, wherein the abbreviations have the usual meaning in the art, temperatures are indicated in degrees centigrade (° C.). NMR spectral data were recorded on a Bruker AMX 500 spectrometer in $CDCl_3$ at 500 MHz for $^1H$ and at 125.8 MHz for $^{13}C$ if not indicated otherwise, the chemical displacements δ are indicated in ppm with respect to $Si(CH_3)_4$ as the standard, the coupling constants J are expressed in Hz (br.=broad peak). Reactions were carried out in standard glassware under $N_2$. Commercially available reagents and solvents were used without further purification if not stated otherwise. Although specific conformations or configurations are indicated for some of the compounds, this is not meant to limit the use of these compounds to the isomers described. According to the invention, all possible conformation or configuration isomers are expected to have a similar effect.

Example 1

Preparation of Compounds According to Formula (I)

(a) Synthesis of 2-phenylethyl 2-oxo-2-phenylacetate (Compound O1)

At 0° C., a solution of N,N'-dicyclohexylcarbodiimide (DCC, 5.54 g, 27 mmol) in dichloromethane (30 mL) was added dropwise to a solution of 4-dimethylaminopyridine (DMAP, 0.28 g, 0.3 mmol), 2-phenylethanol (5.00 g, 41 mmol) and 2-oxo-2-phenylacetic acid (benzoylformic acid, 3.43 g, 23 mmol) in dichloromethane (140 mL). After stirring for 10 min, the reaction mixture was left warming to room temperature. After 6 h, the reaction mixture was filtered through Celite®, extracted with diethyl ether (2×), washed with water (3×), an aqueous solution of HCl (10%, 3×) and a saturated aqueous solution of $NaHCO_3$. The organic phase was dried ($Na_2SO_4$), filtered and concentrated. Column chromatography ($SiO_2$, n-heptane/diethyl ether 8:2 to 7:3) afforded 5.52 g (94%) of the title compound.

$^1H$-NMR: 7.88-7.83 (m, 2H), 7.65-7.60 (m, 1H), 7.48-7.42 (m, 2H), 7.35-7.29 (m, 2H), 7.29-7.23 (m, 3H), 4.62 (t, J=7.1, 2H), 3.09 (t, J=7.1, 2H).

$^{13}C$-NMR: 186.28, 163.72, 136.95, 134.87, 132.33, 130.02, 129.01, 128.85, 128.69, 126.86, 66.40, 34.94.

(b) Synthesis of (E)-oct-2-en-4-yl 2-oxo-2-phenylacetate (Compound O2)

Under nitrogen a dispersion of $LiAlH_4$ (1.8 g, 47.4 mmol) in tetrahydrofuran (THF, 50 mL) was cooled on an ice bath. (E)-Oct-2-en-4-one (10.0 g, 79.2 mmol) in THF (50 mL) was added dropwise during 30 min while keeping the reaction temperature below 5° C. After stirring at room temperature for 1 h, the mixture was cooled at 0° C. with an ice bath and water (1.8 g) was added very slowly while keeping the reaction temperature below 7° C. Then an aqueous solution of NaOH (10%, 1.8 g) and water (5.4 g) were added. The ice bath was removed and the mixture was stirred for 1 h. A white precipitate was slowly formed. Sodium sulphate (10.0 g) was added and the reaction mixture filtered. THF was removed under reduced pressure (40° C., 4 mbar, 2 h) to give 9.59 g (90%) of (E)-oct-2-en-4-ol.

$^1$H-NMR: 5.70-5.60 (m, 1H), 5.52-5.44 (m, 1H), 4.02 (q, J=6.7, 1H), 1.70 (dd, J=6.4, 1.3, 3H), 1.63-1.41 (m, 3H), 1.39-1.23 (m, 4H), 0.90 (t, J=7.1, 3H). $^{13}$C-NMR: 134.46, 126.68, 73.17, 37.03, 27.69, 22.66, 17.68, 14.07.

At 0° C., a solution of DCC (8.34 g, 43 mmol) in dichloromethane (25 mL) was added dropwise to a solution of (E)-oct-2-en-4-ol (5.00 g, 39 mmol), 2-oxo-2-phenylacetic acid (8.78 g, 59 mmol) and DMAP (3.81 g, 31 mmol), in dichloromethane (30 mL). The reaction mixture was left warming to room temperature. After stirring for 18 h, the reaction mixture was filtered through sintered glass, rinsed with dichloromethane (20 mL), and concentrated. The residue was taken up in ethyl acetate (70 mL) and washed with an aqueous solution of HCl (10%, 50 mL), a saturated aqueous solution of NaCl (50 mL), an aqueous solution of $NaHCO_3$ (10%, 50 mL) and again with a saturated aqueous solution of NaCl (50 mL). The organic phase was dried ($Na_2SO_4$), filtered and concentrated. Column chromatography ($SiO_2$, n-pentane/ethyl acetate 8:2) afforded 7.60 g (75%) of the title compound.

$^1$H-NMR: 8.01-7.96 (m, 2H), 7.68-7.62 (m, 1H), 7.54-7.48 (m, 2H), 5.94-5.85 (m, 1H), 5.56-5.44 (m, 2H), 1.84-1.63 (m, 5H), 1.41-1.29 (m, 4H), 0.91 (t, J=7.1, 3H).

$^{13}$C-NMR: 186.73, 163.57, 134.77, 132.61, 131.17, 129.99, 128.86, 128.61, 77.90, 34.08, 27.32, 22.38, 17.78, 13.95.

Example 2

Method to Classify Perfumery Raw Materials into Groups A and B

Solutions of ethyl 2-oxo-2-phenylacetate (3.0 g $L^{-1}$, origin: Alfa Aesar) and the fragrance raw material(s) to be tested (3.0 g $L^{-1}$) in undegassed acetonitrile were mixed in a GC vial (0.5 mL each) to afford solutions of 1.5 g $L^{-1}$ of each component at a weight ratio of 1:1. All fragrance raw materials were tested as obtained from commercial sources without further purification. Fragrance raw materials commercialized as mixtures of isomers were tested as obtained in a weight ratio of 1:1 with respect to the 2-oxoacetate. Each sample was prepared in duplicate. One of the samples served as the reference (100%), the other sample was irradiated.

Photoirradiations were performed with a Sanalux SAN-40 lamp, equipped with Philips PL-L 36W/09/4P light bulbs, at 3.1 mW $cm^{-2}$ of UVA light. The light energy was monitored with an Ahlborn Almemo 2690-8A measuring device, equipped with a FLA 603 UV14 UVA sensor. The UV lamp was preheated for 1 h and placed at a distance to the samples in order to obtain the desired constant irradiation energy of 3.1 mW $cm^{-2}$.

The amount of degradation of ethyl 2-oxo-2-phenylacetate in the presence of a given perfumery raw material was determined by analytical gas chromatography (GC). The first of the two samples was injected to the GC without irradiation; the second sample was irradiated for 40 min at 3.1 mW $cm^{-2}$ (as outlined before) before injection. The amount of degradation corresponds to the percentage of the recorded GC peak area obtained for ethyl 2-oxo-2-phenylacetate remaining after 40 min of irradiation with respect to the GC peak area of ethyl 2-oxo-2-phenylacetate recorded before irradiation. In the absence of perfumery raw materials, ethyl 2-oxo-2-phenylacetate was found to degrade to 19.9 (±7.6)% under these conditions.

If the peak area of ethyl 2-oxo-2-phenylacetate recorded after irradiation for 40 min in the presence of a given perfumery raw material decreased to a value of 50% or less with respect to the non-irradiated sample, the corresponding perfumery raw material is considered as being part of Group A. If the peak area of ethyl 2-oxo-2-phenylacetate after irradiation for 40 min in the presence of a given perfumery raw material decreased to a value above 50%, the corresponding perfumery raw material is considered as being part of Group B.

Analytical GC before and after irradiation was performed on an Agilent Technologies 7890A GC System equipped with an Agilent Technologies 7683B Series injector and a flame ionization detector (FID). Samples (5 μL, split ratio 50:1) were eluted with helium (2.4 mL $min^{-1}$) on an Agilent HP-5 capillary column (30 m, 0.32 mm i.d., film 0.25 μm) at 60° C. for 1 min, and then heated to 250° C. at 10° C. $min^{-1}$.

The following results obtained for the screening of different perfumery raw materials are summarized in Table 1.

TABLE 1

Classification of a selection of perfumery raw materials into Groups A and B.

| Name of perfumery raw material | Amount of remaining ethyl 2-oxo-2-phenylacetate after irradiation | Group |
|---|---|---|
| Benzaldehyde | 23% | A |
| Benzo[d][1,3]dioxole-5-carbaldehyde | 54% | B |
| Benzyl benzoate | 24% | A |
| (E)-1-(Benzyloxy)-2-methoxy-4-(prop-1-en-1-yl)benzene | 66% | B |
| 2H-Chromen-2-one | 78% | B |
| 4-Cyclohexyl-2-methyl-2-butanol | 24% | A |
| Diethyl 1,4-cyclohexanedicarboxylate | 19% | A |
| 1,2-Dimethoxy-4-[(1E)-1-propen-1-yl]benzene | 73% | B |
| 2,4-Dimethyl-3-cyclohexene-1-carbaldehyde | 21% | A |
| 1-(5,5-Di methyl-1-cyclohexen-1-yl)-4-penten-1-one | 23% | A |
| 2,6-Dimethyl-2-heptanol | 32% | A |
| 3,7-Dimethyl-2,6-and 3,6-nonadienenitrile | 17% | A |
| (E)-3,7-Dimethyl-2,6-octadienol | 17% | A |
| 3,7-Dimethyl-1,6-octadien-3-ol | 16% | A |
| 3,7-Dimethyl-6-octenenitrile | 23% | A |
| 2,6-Dimethyl-7-octen-2-ol | 32% | A |
| 1,5-Dimethyl-1-vinyl-4-hexenyl (E)-3-phenylpropenoate | 61% | B |
| Ethyl 2-methylpentanoate | 15% | A |
| (2E)-2-Ethyl-4-[2,2,3-trimethyl-3-cyclopenten-1-yl]-2-buten-1-ol | 38% | A |
| 5-Heptyldihydro-2(3H)-furanone | 17% | A |
| 4,6,6,7,8,8-Hexamethyl-1,3,4,6,7,8-hexahydrocyclopenta[g]isochromene | 15% | A |
| (E)-2-Hexyl-3-phenyl-2-propenal | 80% | B |
| 4-(4-Hydroxy-3-methoxyphenyl)-2-butanone | 78% | B |
| 2-Isobutylquinoline | 70% | B |
| 3-(4-Isopropylphenyl)-2-methylpropanal | 14% | A |
| 2-Methoxynaphthalene | 87% | B |
| 2-Methoxy-4-(2-propen-1-yl)phenol | 80% | B |
| 2-Methoxy-4-[(1E)-1-propen-1-yl]phenol | 80% | B |
| 2-Methoxy-4-propylphenol | 78% | B |
| Methyl 2-aminobenzoate | 99% | B |
| Methyl N-[3-(4-tert-butylphenyl)-2-methyl-1-propenyl]anthranilate | 89% | B |
| Methyl 2,2-dimethyl-6-methylidenecyclohexane-carboxylate | 24% | A |
| Methyl 2-(methylamino)benzoate | 99% | B |
| 2-Methyl-3-[4-(2-methyl-2-propanyl)phenyl] propanal | 15% | A |

TABLE 1-continued

| Classification of a selection of perfumery raw materials into Groups A and B. | | |
|---|---|---|
| Name of perfumery raw material | Amount of remaining ethyl 2-oxo-2-phenylacetate after irradiation | Group |
| 4-Methyl-2-(2-methyl-1-propen-1-yl)tetrahydro-2H-pyran | 23% | A |
| Methyl 2-(3-oxo-2-pentylcyclopentyl)acetate | 17% | A |
| 3-Methyl-5-phenyl-1-pentanol | 19% | A |
| 2-(2-Methyl-2-propanyl)cyclohexyl acetate | 20% | A |
| 4-(2-Methyl-2-propanyl)cyclohexyl acetate | 16% | A |
| 1-Methyl-4-(prop-1-en-2-yl)cyclohex-1-ene | 28% | A |
| 6-Methyl-1,2,3,4-tetrahydroquinoline | 93% | B |
| 1-(Naphthalen-2-yl)ethan-1-one | 91% | B |
| (E)-Oct-2-en-4-one | 31% | A |
| 1-Oxa-12-and 13-cyclohexadecen-2-one | 15% | A |
| 1,1'-Oxydibenzene | 16% | A |
| (E)-2-Pentyl-3-phenyl-2-propenal | 92% | B |
| 2-Phenylacetaldehyde | 26% | A |
| 3-Phenylbutanal | 31% | A |
| (Z)-2-Phenyl-2-hexenenitrile | 62% | B |
| (E)-3-Phenyl-2-propen-1-ol | 62% | B |
| 4-(2-Propanyl)cyclohexyl]methanol | 19% | A |
| Tetrahydro-2-isobutyl-4-methyl-4(2H)-pyranol | 22% | A |
| (2E)-1-(2,6,6-Trimethyl-1,3-cyclohexadien-1-yl)-2-buten-1-one | 91% | B |
| (2E)-1-[2,6,6-Trimethyl-1-cyclohexen-1-yl]-2-buten-1-one | 28% | A |
| (2E)-1-(2,6,6-Trimethyl-2-cyclohexen-1-yl)-2-buten-1-one | 28% | A |
| (3E)-4-(2,6,6-Trimethyl-1-cyclohexen-1-yl)-3-buten-2-one | 74% | B |
| 1,3,5-Undecatriene | 36% | A |

As one can see, different perfume raw materials interfere differently with the light-induced degradation of 2-oxoacetates. The higher the percentage of the remaining ethyl 2-oxo-2-phenylacetate after irradiation, the stronger is the impact of the respective perfume raw material on the photoreaction and the less of it should be used.

Example 3

Preparation of Model Perfumes Using Perfumery Raw Materials of Groups A and B The following model perfumes were prepared:

| Name of perfumery raw material | Amount in weight-% | Group |
|---|---|---|
| Model Perfume 1 (P1) | | |
| Methyl 2,2-dimethyl-6-methylidenecyclohexane-carboxylate | 20% | A |
| 2-(2-Methyl-2-propanyl)cyclohexyl acetate | 20% | A |
| 4-tert-Butyl-1-cyclohexyl acetate | 20% | A |
| (Z)-2-Phenyl-2-hexenenitrile | 20% | B |
| 3-(4-Isopropylphenyl)-2-methylpropanal | 20% | A |
| Sum | 100% | A: 80%<br>B: 20% |
| Model Perfume 2 (P2) | | |
| (E)-2-Hexyl-3-phenyl-2-propenal | 66% | B |
| 2H-Chromen-2-one | 2% | B |

-continued

| Name of perfumery raw material | Amount in weight-% | Group |
|---|---|---|
| 1,1'-Oxydibenzene | 2% | A |
| Benzo[d][1,3]dioxole-5-carbaldehyde | 15% | B |
| (Z)-2-Phenyl-2-hexenenitrile | 15% | B |
| Sum | 100% | A: 2%<br>B: 98% |
| Model Perfume 3 (P3) | | |
| 5-Heptyldihydro-2(3H)-furanone | 40% | A |
| Methyl 2-(3-oxo-2-pentylcyclopentyl)acetate | 20% | A |
| 1-Oxa-12- and 13-cyclohexadecen-2-one | 20% | A |
| Ethyl 2-methylpentanoate | 10% | A |
| Diethyl 1,4-cyclohexanedicarboxylate | 10% | A |
| Sum | 100% | A: 100%<br>B: 0% |

Example 4

Preparation of Core-Shell Microcapsules A and B Using 2-Oxoacetates of Formula (I) and/or Perfumery Raw Materials of Groups A and B as the Oil Phase to be Encapsulated Core-shell microcapsules were prepared according to the following general protocol:

| Ingredient | Capsules [%] |
|---|---|
| Oil Phase | 30.9 |
| Model Perfume according to Example 3 and/or 2-oxoacetate derivative of formula (I) | 30.28 |
| Trimethylol propane adduct of xylylene diisocyanate[1)] | 0.62 |
| Water phase | 69.1 |
| Acrylamide and acrylic acid copolymer[2)] | 4.7 |
| Melamine-formaldehyde resins[3)] | 1.25[3)] |
| Water | 51.75 |
| Sodium hydroxide | 0.5 |
| Acetic acid | 0.2 |
| Acrylamidopropyltrimonium chloride/acrylamide copolymer [4)] | 10.7 |
| Total | 100 |

[1)]Takenate ® D110N (75% active solution in ethyl acetate)
[2)]Alcapsol from Ciba, 20% solution in water
[3)]90/10 blend of Cymel 385 & Cymel 9370 from Cytec, both 70% solution in water
[4)] Salcare SC60 from Ciba, 3% solution in water The oil phase was prepared by admixing a polyisocyanate (trimethylol propane adduct of xylylene diisocyanate, Takenate® D-110N, origin: Mitsui Chemicals) with a core oil. The oil phase consisted of 2% Takenate® D-110N and 98% of core oil.

To make the capsules slurry, the acrylamide and acrylic acid copolymer and the blend of the two melamine-formaldehyde resins were dissolved in water to form the water phase. Then the oil phase was added into this solution and the pH was regulated to 5 with acetic acid. The temperature was raised to 80° C. for 2 h to allow the curing of the capsules. A 3% Salcare SC60 (acrylamidopropyltrimonium chloride/acrylamide copolymer) solution in water was then added into the mixture at 80° C. and was allowed to react for 1 h at 80° C. Then a solution of ethylene urea (50% wt in water) was added to scavenge residual free formaldehyde and the slurry was left to cool down to room temperature. The final pH was adjusted to 7 with sodium hydroxide.

Microcapsules C0 were prepared according to the general protocol, using 2-phenylethyl 2-oxo-2-phenylacetate (O1, 28.35 g, prepared as described in Example 1a) as the oil phase to be encapsulated. Flow particle image analysis (FPIA) revealed an average capsule diameter of 13.5 μm; thermogravimetric analysis (TGA) indicated an oil content of 29.7 wt-%.

Microcapsules C1 were prepared according to the general protocol, using a mixture of 2-phenylethyl 2-oxo-2-phenylacetate (O1, 4.71 g) and Model Perfume 1 (P1, 23.61 g) as the oil phase to be encapsulated. FPIA revealed an average capsule diameter of 12.7 μm; TGA indicated an oil content of 30.4 wt-%.

Microcapsules C2 were prepared according to the general protocol, using a mixture of 2-phenylethyl 2-oxo-2-phenylacetate (O1, 7.12 g) and Model Perfume 2 (P2, 21.31 g) as the oil phase to be encapsulated. FPIA revealed an average capsule diameter of 12.8 μm; TGA indicated an oil content of 28.8 wt-%.

Microcapsules C3 were prepared according to the general protocol, using a mixture of 2-phenylethyl 2-oxo-2-phenylacetate (O1, 9.48 g) and model Perfume 3 (P3, 18.95 g) as the oil phase to be encapsulated, and copolymer RSL9500 (origin: SNF, France) as acrylamide and acrylic acid copolymer. FPIA revealed an average capsule diameter of 10.2 μm; TGA indicated an oil content of 29.8 wt-%.

Microcapsules D1 were prepared according to the general protocol, using Model Perfume 1 (P1, 28.12 g) as the oil phase to be encapsulated. FPIA revealed an average capsule diameter of 11.0 μm; TGA indicated an oil content of 28.9 wt-%.

Microcapsules D2 were prepared according to the general protocol, using Model Perfume 2 (P2, 28.33 g) as the oil phase to be encapsulated. FPIA revealed an average capsule diameter of 16.1 μm; TGA indicated an oil content of 28.9 wt-%.

Microcapsules D3 were prepared according to the general protocol, using Model Perfume 3 (P3, 28.31 g) as the oil phase to be encapsulated and copolymer RSL9500 (origin: SNF, France) as acrylamide and acrylic acid copolymer. FPIA revealed an average capsule diameter of 11.0 μm; TGA indicated an oil content of 29.1 wt-%.

Further core-shell microcapsules were prepared according to the following protocol:

Preparation of polyamide Microcapsules C4: Sodium caseinate (2.0 g) was dispersed in benzyl benzoate (10.0 g, perfumery raw material of Group A) and the dispersion was maintained under stirring at 60° C. for 30 min, and then added to 2-phenylethyl 2-oxo-2-phenylacetate (O1, 25.0 g) at room temperature. Benzene-1,3,5-tricarbonyle chloride (1.7 g) was solubilized at 60° C. for 1 min. Both oil phases were mixed together, stirred at room temperature for 30 s, and mixed with a solution of L-Lysine (2.5 g) in tap water (94.0 g). The reaction mixture was stirred with an Ultra Turrax at 24,000 rpm for 30 s to afford an emulsion. Ethylene diamine (0.12 g) and diethylene triamine (0.21 g) were dissolved in tap water (5.0 g) and this solution was added dropwise to the emulsion over the period of five 25 minutes. The reaction mixture was stirred at 60° C. for 4 h to afford a white dispersion.

Microcapsules C5 were prepared according to the protocol for the preparation of Microcapsules C4 by replacing benzyl benzoate with 1,2-dimethoxy-4-[(1E)-1-propen-1-yl] benzene (perfumery raw material of Group B).

Microcapsules containing a 2-oxoacetate of formula (I) are designated as Microcapsules C0, C1, C2, C3, C4, C5, etc. microcapsules not containing a 2-oxoacetate of formula (I) are designated as Microcapsules D1, D2, D3, etc.

Example 5

Evaluation of the Performance of Perfume Systems According to the Present Invention by Dynamic Headspace Analysis Perfume systems according to the invention, containing microcapsules A and/or B and/or free perfume oil, were dispersed in aqueous sodium lauryl ether sulfate (SLES, 3 wt-%, 12.2 g) to contain a total amount of 2-oxoacetate of 5.8 mg in the final dispersion. The amount of perfumery raw materials in the different dispersions was then adjusted to always correspond to the same ratio with respect to the amount of 2-oxoacetate. For example, Microcapsules C1 contained 30.4 wt-% of oil, composed of 16.6% of 2-phenylethyl 2-oxo-2-phenylacetate (O1) and 83.4% of Model Perfume 1 (P1, consisting of 5 perfumery raw materials each at 16.6%). A dispersion obtained from 114.1 mg of Microcapsules C1 and 12.2 g of SLES thus contained 5.8 mg of 2-phenylethyl 2-oxo-2-phenylacetate and 28.9 mg of Model Perfume 1. Equivalent dispersions containing the same total amounts of 2-phenylethyl 2-oxo-2-phenylacetate (5.8 mg) and Model Perfume 1 (28.9 mg) were prepared by adding Microcapsules C0 (19.5 mg) and Microcapsules D1 (100.0 mg) to 12.2 g of SLES or by adding free 2-phenylethyl 2-oxo-2-phenylacetate (5.8 mg) and Microcapsules D1 (100.0 mg) to 12.2 g of SLES. Other samples were prepared accordingly.

The dispersions (250 mg) were then pipetted onto glass slides (13×4 cm) and left drying overnight in the dark. Each glass plate was then covered with a second glass plate. The two plates were rubbed against each other by pressing them firmly together while moving them 5× from left to right and 5× from top to bottom. The two plates were then separated and placed inside a home-made headspace sampling cell (625 mL) by orienting them towards the lamp. An air flow of 200 mL min-, filtered through activated charcoal and humidified through a saturated aqueous solution of NaCl was aspirated through the cell. The system was left equilibrating for 10 min by adsorbing the volatiles onto a waste poly(2,6-diphenyl-p-phenylene oxide (Tenax® TA, 100 mg) cartridge and then for 5 min onto a clean cartridge (first data point). The lamp was switched on, and the volatiles were adsorbed for 5 min onto a waste Tenax®, then 5× for 5 min onto clean Tenax® cartridges (data points 2-6). Then the volatiles were adsorbed onto a waste Tenax® cartridge for 5 min and onto a clean Tenax® cartridge for 5 min (3×, data points 7-9). Finally the volatiles were adsorbed onto a waste Tenax® cartridge for 25 min and onto a clean Tenax® cartridge for 5 min (data point 10). Waste Tenax® cartridges were discarded, clean Tenax® cartridges were desorbed on a Perkin Elmer TurboMatrix ATD thermodesorber connected to an Agilent Technologies 7890A GC System equipped with a FID. The volatiles were eluted with He on a HP-5 capillary column (30 m×0.32 μm, film 0.25 μm) using a temperature gradient from 60° C. to 200 or 260° C. at 15° C. min. Headspace concentrations (in ng $L^{-1}$) were obtained by external standard calibration, by injecting solutions of known amounts of volatiles onto clean Tenax® cartridges and desorbing them as described before.

Photoirradiations were carried out with a UVA lamp (360 nm) at a light energy of 1.6 mW $cm^{-2}$, which was checked with an Ahlborn Almemo 2690-8A measuring device connected to a FLA 603 UV14 UVA sensor.

The perfume systems listed in the table below were prepared as outlined before and evaluated on glass slides by dynamic headspace analysis during photoirradiation (UVA light at 1.6 mW $cm^{-2}$); values in brackets indicate the amount of perfumery raw materials of Group B for each part of the perfume system. Headspace concentrations of fragrances released from 2-oxoacetate derivatives of formula (I) as part of the different perfume systems recorded after 35 min (=after 20 min of irradiation, data point 4) are indicated.

| Entry | Microcapsule A | Microcapsule B | Free perfume oil | Headspace concentration [ng $L^{-1}$] | Denomination in FIG. 1 |
|---|---|---|---|---|---|
| 1 | C0 (0%) | D1 (20%) | — | 156.7 | A (0%) B (20%) —□— |
| 2 | C0 (0%) | D2 (98%) | — | 69.3 | A (0%) B (98%) —■— |
| 3 | C0 (0%) | D3 (0%) | — | 314.4 | A (0%) B (0%) ·····□····· |
| 4 | C1 (17%) | — | — | 138.2 | AP (17%) —◊— |
| 5 | C2 (73%) | — | — | 57.7 | AP (73%) —♦— |
| 6 | C3 (0%) | — | — | 393.4 | AP (0%) ·····◊····· |
| 7 | C0 (0%) | — | P1 (20%) | 301.8 | A (0%) P (20%) —○— |
| 8 | C0 (0%) | — | P2 (98%) | 77.3 | A (0%) P (98%) —■— |
| 9 | C0 (0%) | — | P3 (0%) | 364.4 | A (0%) P (0%) ·····○····· |
| 10 | D1 (20%) | — | O1 | 79.7 | B (20%) P (0%) —Δ— |
| 11 | D2 (98%) | — | O1 | 38.8 | B (98%) P (0%) —▲— |
| 12 | D3 (0%) | — | O1 | 310.8 | B (0%) P (0%) ·····Δ····· |
| 13 | D3 (0%) | — | O2 | 2343.1 | B (0%) P (0%) data not shown in FIG. 1 |

The headspace analyses showed that, essentially, the different fragrance raw materials of the Model Perfumes evaporated more slowly (higher headspace concentrations) when they were encapsulated (and thus released by rubbing before the experiment) and more rapidly (lower headspace concentrations) when they were part of the free perfume oil and could thus evaporate overnight. Under the present conditions, the evaporation of the fragrance raw materials was not much influenced by the light-induced cleavage of the 2-oxoacetate.

On the other hand, the light-induced generation of 2-phenylacetaldehyde from 2-phenylethyl 2-oxo-2-phenylacetate (O1) depended on the presence of perfumery raw materials of Group B. The headspace concentrations of 2-phenylacetaldehyde measured for the different perfume systems outlined above are summarized in FIG. 1.

FIG. 1 displays dynamic headspace concentrations of 2-phenylacetaldehyde generated from 2-phenylethyl 2-oxo-2-phenylacetate (O1) upon photoirradiation of different perfume systems containing various amounts of perfumery raw materials of Group B (indicated in brackets) in Microcapsules A or B or in the free perfume oil (P). Empty symbols and continuous lines represent the formation of 2-phenylacetaldehyde in the presence of Model Perfume 1 (P1), which contains less than 30% of perfumery raw materials of Group B, full symbols and continuous lines represent the formation of 2-phenylacetaldehyde in the presence of Model Perfume 2 (P2), which contains more than 30% of perfumery raw materials of Group B and empty symbols and dotted lines represent the formation of 2-phenylacetaldehyde in the presence of Model Perfume 1 (P3), which contains no (0%) perfumery raw materials of Group B.

The data in FIG. 1 show that perfume systems containing more than 30% of perfumery raw materials of Group B (full symbols and continuous lines) release significantly less 2-phenylacetaldehyde from 2-phenylethyl 2-oxo-2-phenylacetate than perfume systems containing less than 30% of perfumery raw materials of Group B (empty symbols and continuous lines) and considerably less 2-phenylacetaldehyde than perfume systems containing no perfumery raw materials of Group B (empty symbols and dotted lines).

Furthermore, one can see that perfumery raw materials of Group B are preferentially part of the free perfume oil (circles, e.g. —○—) ) rather than being encapsulated in microcapsules A (rhombi, e.g. —◊—) ) or B (squares, e.g. —□—). ).

As a further reference, photoirradiation of 2-phenylethyl 2-oxo-2-phenylacetate (O1) alone under the same conditions generated 300.8 ng/L of 2-phenylacetaldehyde after sampling for 35 min (data not shown in FIG. 1). This value is in the same order of magnitude as those recorded for a perfume system that contained no encapsulated perfume raw materials of Group B (see Entry 12 in the table above).

Irradiation of a perfume system consisting of 2-oxoacetate O2 and Microcapsules D3, containing no perfume raw materials of Group B, which was prepared and irradiated under the same conditions described before, showed a strong release of (E)-oct-2-en-4-one (see Entry 13 in the table above). Again, the recorded headspace concentrations of (E)-oct-2-en-4-one released from this perfume system were hereby in the same order of magnitude as those measured for the irradiation of 2-oxoacetate O2 alone (2937.9 ng/L after 35 min of sampling). This demonstrates that different 2-oxoacetates of formula (I) releasing different perfumery aldehydes or ketones can be used for the preparation of the perfume systems.

It should be noted that the absolute headspace concentrations of fragrances released upon photoirradion from structurally different 2-oxoacetates of formula (I) vary from one compound to another. Comparisons should thus be made within series using the same compound of formula (I).

Example 6

Evaluation of the Performance of Perfume Systems According to the Present Invention by Dynamic Headspace Analysis Perfume systems containing microcapsules A according to the invention were dispersed in aqueous sodium lauryl ether sulfate (SLES, 3 wt-%, 12.2 g) to contain a total amount of 2-oxoacetate of 5.7 mg in the final dispersion. The dispersions (250 mg) were then pipetted onto glass slides (13×4 cm) and treated as described in Example 5.

The perfume systems listed in the table below were prepared and analyzed by dynamic headspace analysis on glass slides during photoirradiation (UVA light at 1.6 mW $cm^{-2}$) as outlined in Example 5; values in brackets indicate the amount of perfumery raw materials of Group B for each part of the perfume system. Headspace concentrations of 2-phenylacetaldehyde released from 2-oxoacetate O1 as part of the different perfume systems recorded after 35 min (=after 20 min of irradiation, data point 4) are indicated.

Figure 2:
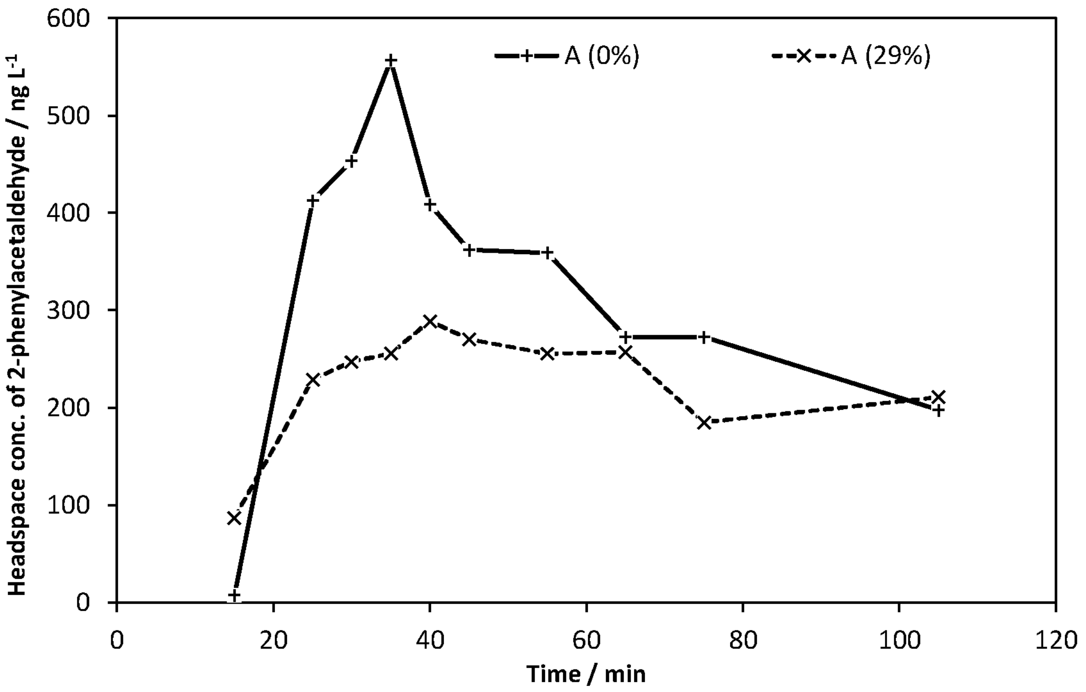
FIG. 2: Dynamic headspace concentrations of 2-phenylacetaldehyde generated from 2-phenylethyl 2-oxo-2-phenylacetate (O1) according to formula (I) upon photoirradiation of perfume systems containing various amounts of perfumery raw materials of Group B in microcapsules A (see Example 6).

| Entry | Microcapsule A | Microcapsule B | Free perfume oil | Headspace concentration [ng $L^{-1}$] | Denomination in FIG. 2 |
|---|---|---|---|---|---|
| 1 | C4 (0%) | — | — | 556.9 | A (0%) —+— |
| 2 | C5 (29%) | — | — | 255.9 | A (29%) - - -x- - - |

FIG. 2 displays dynamic headspace concentrations of 2-phenylacetaldehyde generated from 2-oxoacetate O1 upon photoirradiation of different perfume systems containing 0% or 29% of perfumery raw materials of Group B (indicated in brackets) in Microcapsules A.

The data show that the presence of perfumery raw materials of Group B resulted in lower headspace concentrations of 2-phenylacetaldehyde released into the headspace than the comparable sample containing no perfumery raw materials of Group B.

Example 7

Preparation of Liquid Detergent Formulations Comprising an Invention's Perfume System Perfume systems according to the present invention, such as those described in Examples or 6 as non-limiting examples, are dispersed under gentle shaking in a liquid detergent formulation with a typical composition as described below to obtain a total amount of encapsulated and free perfume oil of 0.10 to 0.80% in the final product.

| Ingredients | Amount [wt %] |
|---|---|
| Sodium $C_{14-17}$ Alkyl Sec Sulfonate[1] | 7.0 |
| Fatty acids, $C_{12-18}$ and Cis-unsaturated[2] | 7.5 |
| $C_{12/14}$ fatty alcohol polyglycol ether with 7 mol EO[3] | 17.0 |
| Triethanolamine | 7.5 |
| Propylene glycol | 11.0 |
| Citric acid | 6.5 |
| Potassium hydroxyde | 9.5 |
| Protease | 0.2 |
| Amylase | 0.2 |

-continued

| Ingredients | Amount [wt %] |
|---|---|
| Mannanase | 0.2 |
| Acrylates/Steareth-20 methacrylate structuring crosspolymer[4] | 6.0 |
| Deionized water | 27.4 |
| Total | 100.0 |

[1] Hostapur ® SAS 60; origin: Clariant
[2] Edenor ® K 12-18; origin: Cognis
[3] Genapol ® LA 070; origin: Clariant
[4] Aculyn ® 88; origin: Dow Chemicals

Example 8

Preparation of Fabric Softener Formulations Comprising an Invention's Perfume System Perfume systems according to the present invention, such as those described in Examples 50r 6 as non-limiting examples, are dispersed under gentle shaking in a fabric softener formulation with a typical composition as described below to obtain a total amount of encapsulated and free perfume oil of 0.20 to 0.80% in the final product.

| Ingredients | Amount [wt %] |
|---|---|
| Stepantex ® VL 90A[1] | 8.88 |
| Calcium chloride (10% aqueous solution) | 0.36 |
| Proxel ® GXL[2] | 0.04 |
| Deionized water | 90.72 |
| Total | 100.00 |

[1] Origin: Stepan
[2] Origin: Avecia

Example 9

Preparation of all-Purpose Cleaner Formulations Comprising an Invention's Perfume System Perfume systems according to the present invention, such as those described in Examples 5 or 6 as non-limiting examples, are dispersed under gentle shaking in an all-purpose cleaner formulation with a typical composition as described below to obtain a total amount of encapsulated and free perfume oil of 0.30 to 0.80% in the final product.

| Ingredients | Amount [wt %] |
|---|---|
| Ethoxylated alcohol ($C_9$-$C_{11}$, 8 EO)[1] | 20.0 |
| Sodium dodecyl benzene sulfonate[2] | 16.0 |
| Sodiumcumene sulfonate[3] | |

-continued

| Ingredients | Amount [wt %] |
|---|---|
| Methyl chloro isothiazolinone/ methyl isothiazolinone 3.3:1[4)] | 0.8 |
| Deionized water | 55.2 |
| Total | 100.0 |

1)Neodol ®91-8; origin: Shell Chemicals
2)Biosoft ® D-40; origin: Stepan
3)Stepanate ® SCS; origin: Stepan
4)Kathon ® CG; origin: Dow Chemicals

Example 10

Preparation of Hand Dishwash Formulations Comprising an Invention's Perfume System A typical unperfumed hand dishwash formulation is prepared from the ingredients listed below by mixing water with sodium hydroxide and diethanolamide. Then the linear alkylbenzene sulfonic acid is added. After neutralizing, the remaining ingredients are added and the pH is adjusted to 7-8 if necessary.

| Ingredients | Amount [wt %] |
|---|---|
| Linear alkylbenzene sulfonic acid[1)] | 20.0 |
| Diethanolamide[2)] | 3.5 |
| Sodium hydroxide (50%)[3)] | 3.4 |
| Secondary alcohol ethoxolate[4)] | 2.5 |
| Sodium xylene sulfonate | 6.3 |
| Water | 64.3 |
| Total | 100.0 |

1)Biosoft ® S-118; origin: Stepan
2)Ninol ® 40-CO; origin: Stepan
3)Stepanate ® SXS; origin: Stepan
4)Tergitol ® 15-S-9; origin: Dow Chemicals Perfume systems according to the present invention, such as those described in Examples 5 or 6 as non-limiting examples, are dispersed under gentle shaking in the unperfumed hand dishwash formulation with a typical composition as described above to obtain a total amount of encapsulated and free perfume oil of 0.10 to 1.00% in the final product.

The invention claimed is:

1. A perfume system comprising:
a) a core-shell microcapsule A,
b) optionally, a core-shell microcapsule B, and
c) optionally, a free perfume oil,
wherein the core of the core-shell microcapsule A and/or the free perfume oil comprises a 2-oxoacetate derivative of formula (I)

(I)

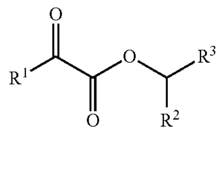

wherein
$R^1$ represents a linear or branched $C_1$ to $C_{22}$ alkyl or alkenyl group, optionally containing one to four oxygen atoms that are not directly connected to the carbonyl group, or a cyclic $C_3$ to $C_8$ alkyl or alkenyl group, optionally containing one to four oxygen atoms that are not directly connected to the carbonyl group, or a phenyl group, optionally substituted with a $C_1$ to $C_4$ alkyl groups;
$R^2$ represents a linear, branched or cyclic $C_1$ to $C_{22}$ hydrocarbon group, optionally containing one to four oxygen atoms and
$R^3$ represents a hydrogen atom or a $C_1$ to $C_{10}$ hydrocarbon group, optionally containing one to two oxygen atoms;
or $R^2$ and $R^3$, when taken together, form a $C_{5-16}$ cycloalkyl, $C_{5-16}$ cycloalkenyl, $C_{4-14}$ heterocycloalkyl or $C_{4-14}$ heterocycloalkenyl group;
wherein the core of the core-shell microcapsule A, the core of the core-shell microcapsule B, or free perfume oil comprises a perfumery raw material of Group B,
wherein the perfumery raw material of Group B is selected from the group consisting of benzo[d][1,3]dioxole-5-carbaldehyde, (E)-1-(benzyloxy)-2-methoxy-4-(prop-1-en-1-yl) benzene, 2H-chromen-2-one, 1,2-dimethoxy-4-[(1E)-1-propen-1-yl]benzene, 1,5-dimethyl-1-vinyl-4-hexenyl (E)-3-phenylpropenoate, (E)-2-hexyl-3-phenyl-2-propenal, 4-(4-hydroxy-3-methoxyphenyl)-2-butanone, 2-isobutylquinoline, 2-methoxynaphthalene, 2-methoxy-4-(2-propen-1-yl) phenol, 2-methoxy-4-[(1E)-1-propen-1-yl] phenol, 2-methoxy-4-propylphenol, methyl 2-aminobenzoate, methyl N-[3-(4-tert-butylphenyl)-2-methyl-1-propenyl] anthranilate, methyl 2-(methylamino)benzoate, 6-methyl-1,2,3,4-tetrahydroquinoline, 1-(naphthalen-2-yl) ethan-1-one, (E)-2-pentyl-3-phenyl-2-propenal, (Z)-2-phenyl-2-hexenenitrile, (E)-3-phenyl-2-propen-1-ol, (2E)-1-(2,6,6-trimethyl-1,3-cyclohexadien-1-yl)-2-buten-1-one and (3E)-4-(2,6,6-trimethyl-1-cyclohexen-1-yl)-3-buten-2-one.

2. The perfume system according to claim 1, wherein the core of the core-shell microcapsule A comprises
at least one 2-oxoacetate derivative of formula (I),
optionally, at least one perfumery raw material of Group A,
at most 20 wt-% of a perfumery raw material of Group B and
optionally, a solvent,
wherein perfumery raw materials of Group A are defined in that 50% or less of ethyl 2-oxo-2-phenylacetate are remaining after irradiation of the perfumery raw material and the ethyl 2-oxo-2-phenylacetate (at 1.5 g $L^{-1}$) in a weight ratio of 1:1 in non-degassed acetonitrile with UVA radiation at 3.1 mW $cm^{-2}$ for 40 min at 25° C.

3. The perfume system according to claim 1, wherein the core of the core-shell microcapsule A does not contain a perfumery raw material of Group B.

4. The perfume system according to claim 1, wherein the core of the core-shell microcapsule B comprises
at least one perfumery raw material of Group A, wherein perfumery raw materials of Group A are defined in that 50% or less of ethyl 2-oxo-2-phenylacetate are remaining after irradiation of the perfumery raw material and the ethyl 2-oxo-2-phenylacetate (at 1.5 g $L^{-1}$) in a weight ratio of 1:1 in non-degassed acetonitrile with UVA radiation at 3.1 mW $cm^{-2}$ for 40 min at 25° C.,
at most 30 wt-% of perfumery raw materials of Group B, and
optionally, a solvent.

5. The perfume system according to claim 1, wherein the free perfume oil comprises
at least one perfumery raw material of Group A, wherein perfumery raw materials of Group A are defined in that 50% or less of ethyl 2-oxo-2-phenylacetate are remaining after irradiation of the perfumery raw material and the ethyl 2-oxo-2-phenylacetate (at 1.5 g $L^{-1}$) in a weight ratio of 1:1 in non-degassed acetonitrile with UVA radiation at 3.1 mW $cm^{-2}$ for 40 min at 25° C., optionally, at least one perfumery raw material of Group B, optionally, at least one 2-oxoacetate derivative of formula (I) and, optionally, a solvent.

6. The perfume system according to claim 1, wherein the free perfume oil comprises not more than 50 wt-% of perfumery raw materials of Group B.

7. The perfume system according to claim 1, wherein the free perfume oil contains from 0.1 to 20 wt-% of the 2-oxoacetate derivative of formula (I).

8. The perfume system according to claim 1, wherein the core of the core-shell microcapsule A and the core of the core-shell microcapsule B is free of the perfumery raw materials of Group B.

9. The perfume system according to claim 2, wherein the perfumery raw material of Group A is selected from the group consisting of allyl 2-(cyclohexyloxy)acetate, allyl 3-cyclohexylpropanoate, allyl heptanoate, allyl hexanoate, benzaldehyde, benzyl acetate, benzyl benzoate, benzyl 2-hydroxybenzoate, 2-cyclohexylethyl acetate, cyclohexyl 2-hydroxybenzoate, 4-cyclohexyl-2-methyl-2-butanol, decanal, diethyl 1,4-cyclohexanedicarboxylate, (2,2-dimethoxyethyl) benzene, 6,6-dimethoxy-2,5,5-trimethyl-2-hexene, 2-(6,6-dimethylbicyclo[3.1.1]hept-2-en-2-yl)ethyl acetate, 2,4-dimethyl-3-cyclohexene-1-carbaldehyde, 1-(5,5-dimethyl-1-cyclohexen-1-yl)-4-penten-1-one, 2,6-dimethyl-2-heptanol, 2,6-dimethyl-5-heptenal, 6,6-dimethyl-2-methylenebicyclo [3.1.1]heptane, 3,7-dimethyl-2,6- and 3,6-nonadienenitrile, 3,7-dimethyl-1,6-nonadien-3-ol, 3,7-dimethyl-2,6-octadienal, (E)-3,7-dimethyl-2,6-octadienol, (Z)-3,7-dimethyl-2,6-octadienol, 3,7-dimethyl-1,6-octadien-3-ol, 3,7-dimethyl-2,6-octadienyl acetate, 3,7-dimethyl-3-octanol, 3,7-dimethyl-6-octenenitrile, 3,7-dimethyl-6-octen-1-ol, 2,6-dimethyl-7-octen-2-ol, 3,7-dimethyl-6-octenyl acetate, 1,1-dimethyl-2-phenylethyl butanoate, 1,1-dimethyl-2-phenylethyl acetate, 3,3-dimethyl-5-[2,2,3-trimethyl-3-cyclopenten-1yl]-4-penten-2-ol, 1,4-dioxacycloheptadecane-5,17-dione, dodecanal, dodecanol, (Z)-4-dodecenal, ethyl butanoate, ethyl 3-hydroxybut-2-enoate, ethyl 2-methylbutanoate, ethyl 2-methyl-1,3-dioxolane-2-acetate, ethyl 2-methylpentanoate, ethyl 3-oxobutanoate, 3-(2- and 4-ethylphenyl)-2,2-dimethylpropanal, (2E)-2-ethyl-4-[2,2,3-trimethyl-3-cyclopenten-1-yl]-2-buten-1-ol, 6-ethyl-2,10,10-trimethyl-1-oxaspiro[4.5]deca-3,6-diene, 5-heptyldihydro-2 (3H)-furanone, 4,6,6,7,8,8-hexamethyl-1,3,4,6,7,8-hexahydrocyclopenta[g] isochromene, 1-(3,5,5,6,8,8-hexamethyl-5,6,7,8-tetrahydro-2-naphthalenyl) ethanone, (Z)-3-hexen-1-ol, (Z)-3-hexenyl acetate, (Z)-3-hexenyl 2-hydroxybenzoate, hexyl acetate, 5-hexyldihydrofuran-2 (3H)-one, hexyl 2-hydroxybenzoate, hexyl 2-methylpropanoate, 3- and 4-(4-hydroxy-4-methylpentyl)-3-cyclohexene-1-carbaldehyde, 1-isopropyl-4-methylbenzene, 2-isopropyl-5-methylcyclohexan-1-ol, isopropyl 2-methylbutanoate, 4-isopropyl-1-methylcyclohexyl acetate, 3-(3-isopropyl-1-phenyl) butanal, 3-(4-isopropylphenyl)-2-methylpropanal, isopropyl tetradecanoate, 4-methoxybenzaldehyde, 1-methoxy-4-methylbenzene, 3-(4-methoxyphenyl)-2-methylpropanal, 4-(2-methoxy-2-propanyl)-1-methylcyclohexene, 1-methoxy-4-(2-propenyl) benzene, 6-methoxy-3,6,8,8-tetramethyloctahydro-1H-3a,7-methanoazulene, methyl benzoate, 7-methyl-2H-1,5-benzodioxepin-3 (4H)-one, 3-methyl-2-buten-1-yl acetate, 2- and 3-methylbutyl acetate, 2- and 3-methylbutyl butyrate, 2-methylbutyl 2-hydroxybenzoate, 2-(4-methylcyclohex-3-enyl) propan-2-ol, 2-(4-methyl-3-cyclohexen-1-yl)-2-propanyl acetate, 2-{2-[4-methyl-3-cyclohexen-1-yl] propyl}cyclopentanone, (E)-4-methyl-3-decen-5-ol, methyl 2,2-dimethyl-6-methylidenecyclohexanecarboxylate, methyl 2,4-dihydroxy-3,6-dimethylbenzoate, 5-methylheptan-3-one oxime, methyl 7-isopropyl-1,4a-dimethyl-1,2,3,4,4a,4b,5,6,7,8,10,10a-dodecahydrophenanthrene-1-carboxylate and methyl 7-isopropyl-1,4a-dimethyltetradecahydrophenanthrene-1-carboxylate, 1-methyl-4-(4-methyl-3-pentenyl)-3-cyclohexene-1-carbaldehyde, 2-methyl-3-[4-(2-methyl-2-propanyl)phenyl]propanal, 4-methyl-2-(2-methyl-1-propen-1-yl)tetrahydro-2H-pyran, methyl 2-octynoate, methyl 2-(3-oxo-2-pentylcyclopentyl)acetate, 4-methyl-4-penten-2-yl 2-methylpropanoate, 3-methyl-5-phenyl-1-pentanol, 5-methyl-2-(2-propanyl)cyclohexanone, 1-methyl-4-(2-propanyl)-1,4-cyclohexadiene, 4-(2-methyl-2-propanyl)cyclohexanol, 2-(2-methyl-2-propanyl)cyclohexyl acetate, 4-(2-methyl-2-propanyl)cyclohexyl acetate, 1-methyl-4-(prop-1-en-2-yl)cyclohex-1-ene, 2-methyl-4-propyl-1,3-oxathiane, (3E)-3-methyl-4-(2,6,6-trimethyl-2-cyclohexan-1-yl)-3-buten-2-one, methyl 2,6,6-trimethyl-3-cyclohexene-1-carboxylate, (3E)-3-methyl-4-(2,6,6-trimethyl-2-cyclohexen-1-yl)-3-buten-2-one and (1E)-1-(2,6,6-trimethyl-2-cyclohexen-1-yl)-1-penten-3-one, 3-methyl-5-(2,2,3-trimethyl-3-cyclopenten-1-yl)-2-pentanol, 2-methylundecanal, 2,6-nonadienal, 2,6-nonadienol, nonanal, octanal, oct-2-en-4-one, oxacyclohexadecan-2-one, 1-oxa-12- and 13-cyclohexadecen-2-one, 1,1'-oxydibenzene, pentyl 2-hydroxybenzoate, 2-phenoxyethanol, 2-phenylacetaldehyde, 3-phenylbutanal, 2-phenylethanol, 2-phenylethyl acetate, phenylmethanol, 4-[(2-propanyl) cyclohexyl]methanol, 7-propyl-2H-benzo[b][1,4] dioxepin-3 (4H)-one, tetrahydro-2-isobutyl-4-methyl-4 (2H)-pyranol, 3a,6,6,9a-tetramethyldodecahydronaphtho[2,1-b]furan, 1-(3,6,8,8-tetramethyl-2,3,4,7,8,8a-hexahydro-1H-3a,7-methanoazulen-5-yl) ethan-1-one, 2,3,6,7- and 2,4,6,8-tetramethylnonan-1-ol, 3,6,8,8-tetramethyloctahydro-1H-3a, 7-methanoazulen-6-yl acetate, 2,2,6,8-tetramethyl-1,2,3,4,4a,5,8,8a-octahydro-1-naphthalenol, 1-(2,3,8,8-tetramethyl-1,2,3,4,5,6,7,8-, 1,2,3,5,6,7,8,8a- and 1,2,3,4,6,7,8,8a-octahydronaphthalen-2-yl) ethan-1-one, tricyclo [5.2.1.0 (2,6)]dec-3- and 4-en-8-yl acetate, 2,2,2-trichloro-1-phenylethyl acetate, tricyclo[5.2.1.0 (2,6)]dec-3- or 4-en-8-yl propanoate, 1,7,7-trimethylbicyclo[2.2.1]heptan-2-ol, 1,7,7-trimethylbicyclo[2.2.1]heptan-2-one, 1,7,7-trimethylbicyclo[2.2.1]heptan-2-yl acetate, 2,6,6-trimethylbicyclo [3.1.1]hept-2-ene, 2-(1,7,7-trimetylbicyclo[2.2.1]hept-2-yl)-1-cyclohexanol, 2-, 3- and 4-(5,5,6-trimethylbicyclo[2.2.1] hept-2-yl)-1-cyclohexanol, (2E)-1-[2,6,6-trimethyl-1-cyclohexen-1-yl]-2-buten-1-one, (2E)-1-(2,6,6-trimethyl-2-cyclohexen-1-yl)-2-buten-1-one, (2E)-1-(2,6,6-trimethyl-3-cyclohexen-1-yl)-2-buten-1-one, 3,8,9-, 4,6,8- and 4,7,9-trimethyldecan-2-ol, 1,3,3-trimethyl-2-oxabicyclo[2.2.2] octane, 2,2,5-trimethyl-5-pentylcyclopentanone, 2,6,6-trimethylspiro[bicyclo[3.1.1]heptane-3,1'-cyclohexane]-2'-en-4'-one, undecanal, 1,3,5-undecatriene and 10-undecenal.

10. A perfuming composition comprising i. the perfume system as defined in claim 1, ii. at least one ingredient selected from the group consisting of a perfumery carrier and a perfumery base; and iii. optionally, at least one perfumery adjuvant.

11. A perfumed consumer product comprising a perfume system according to claim 1, characterized in that the perfumed consumer product is a perfume, a fabric care product, a body-care product, an air care product or a home care product.

12. The perfumed consumer product according to claim 11, characterized in that the perfumed consumer product is a fine perfume, a liquid or solid detergent, a fabric softener, a fabric refresher, an ironing water, a shampoo, a coloring preparation, a hair spray, a deodorant or antiperspirant, a perfumed soap, shower or bath mousse, oil or gel, a hygiene product, an air freshener, a "ready to use" powdered air freshener or a hard-surface detergent.

13. Method for enhancing, conferring, increasing and/or modifying the fragrance properties and/or the fragrance intensity by applying a perfumery system according to claim 1 to a perfumed consumer product.

14. The perfume system according to claim 4, wherein the perfumery raw material of Group A is selected from the group consisting of allyl 2-(cyclohexyloxy)acetate, allyl 3-cyclohexylpropanoate, allyl heptanoate, allyl hexanoate, benzaldehyde, benzyl acetate, benzyl benzoate, benzyl 2-hydroxybenzoate, 2-cyclohexylethyl acetate, cyclohexyl 2-hydroxybenzoate, 4-cyclohexyl-2-methyl-2-butanol, decanal, diethyl 1,4-cyclohexanedicarboxylate, (2,2-dimethoxyethyl) benzene, 6,6-dimethoxy-2,5,5-trimethyl-2-hexene, 2-(6,6-dimethylbicyclo[3.1.1]hept-2-en-2-yl)ethyl acetate, 2,4-dimethyl-3-cyclohexene-1-carbaldehyde, 1-(5,5-dimethyl-1-cyclohexen-1-yl)-4-penten-1-one, 2,6-dimethyl-2-heptanol, 2,6-dimethyl-5-heptenal, 6,6-dimethyl-2-methylenebicyclo [3.1.1]heptane, 3,7-dimethyl-2,6- and 3,6-nonadienenitrile, 3,7-dimethyl-1,6-nonadien-3-ol, 3,7-dimethyl-2,6-octadienal, (E)-3,7-dimethyl-2,6-octadienol, (Z)-3,7-dimethyl-2,6-octadienol, 3,7-dimethyl-1,6-octadien-3-ol, 3,7-dimethyl-2,6-octadienyl acetate, 3,7-dimethyl-3-octanol, 3,7-dimethyl-6-octenenitrile, 3,7-dimethyl-6-octen-1-ol, 2,6-dimethyl-7-octen-2-ol, 3,7-dimethyl-6-octenyl acetate, 1,1-dimethyl-2-phenylethyl butanoate, 1,1-dimethyl-2-phenylethyl acetate, 3,3-dimethyl-5-[2,2,3-trimethyl-3-cyclopenten-1yl]-4-penten-2-ol, 1,4-dioxacycloheptadecane-5,17-dione, dodecanal, dodecanol, (Z)-4-dodecenal, ethyl butanoate, ethyl 3-hydroxybut-2-enoate, ethyl 2-methylbutanoate, ethyl 2-methyl-1,3-dioxolane-2-acetate, ethyl 2-methylpentanoate, ethyl 3-oxobutanoate, 3-(2- and 4-ethylphenyl)-2,2-dimethylpropanal, (2E)-2-ethyl-4-[2,2,3-trimethyl-3-cyclopenten-1-yl]-2-buten-1-ol, 6-ethyl-2,10,10-trimethyl-1-oxaspiro[4.5]deca-3,6-diene, 5-heptyldihydro-2 (3H)-furanone, 4,6,6,7,8,8-hexamethyl-1,3,4,6,7,8-hexahydrocyclopenta[g] isochromene, 1-(3,5,5,6,8,8-hexamethyl-5,6,7,8-tetrahydro-2-naphthalenyl) ethanone, (Z)-3-hexen-1-ol, (Z)-3-hexenyl acetate, (Z)-3-hexenyl 2-hydroxybenzoate, hexyl acetate, 5-hexyldihydrofuran-2 (3H)-one, hexyl 2-hydroxybenzoate, hexyl 2-methylpropanoate, 3- and 4-(4-hydroxy-4-methylpentyl)-3-cyclohexene-1-carbaldehyde, 1-isopropyl-4-methylbenzene, 2-isopropyl-5-methylcyclohexan-1-ol, isopropyl 2-methylbutanoate, 4-isopropyl-1-methylcyclohexyl acetate, 3-(3-isopropyl-1-phenyl) butanal, 3-(4-isopropylphenyl)-2-methylpropanal, isopropyl tetradecanoate, 4-methoxybenzaldehyde, 1-methoxy-4-methylbenzene, 3-(4-methoxyphenyl)-2-methylpropanal, 4-(2-methoxy-2-propanyl)-1-methylcyclohexene, 1-methoxy-4-(2-propenyl) benzene, 6-methoxy-3,6,8,8-tetramethyloctahydro-1H-3a,7-methanoazulene, methyl benzoate, 7-methyl-2H-1,5-benzodioxepin-3 (4H)-one, 3-methyl-2-buten-1-yl acetate, 2- and 3-methylbutyl acetate, 2- and 3-methylbutyl butyrate, 2-methylbutyl 2-hydroxybenzoate, 2-(4-methylcyclohex-3-enyl) propan-2-ol, 2-(4-methyl-3-cyclohexen-1-yl)-2-propanyl acetate, 2-{2-[4-methyl-3-cyclohexen-1-yl] propyl}cyclopentanone, (E)-4-methyl-3-decen-5-ol, methyl 2,2-dimethyl-6-methylidenecyclohexanecarboxylate, methyl 2,4-dihydroxy-3,6-dimethylbenzoate, 5-methylheptan-3-one oxime, methyl 7-isopropyl-1,4a-dimethyl-1,2,3,4,4a,4b,5,6,7,8, 10,10a-dodecahydrophenanthrene-1-carboxylate and methyl 7-isopropyl-1,4a-dimethyltetradecahydrophenanthrene-1-carboxylate, 1-methyl-4-(4-methyl-3-pentenyl)-3-cyclohexene-1-carbaldehyde, 2-methyl-3-[4-(2-methyl-2-propanyl)phenyl]propanal, 4-methyl-2-(2-methyl-1-propen-1-yl)tetrahydro-2H-pyran, methyl 2-octynoate, methyl 2-(3-oxo-2-pentylcyclopentyl)acetate, 4-methyl-4-penten-2-yl 2-methylpropanoate, 3-methyl-5-phenyl-1-pentanol, 5-methyl-2-(2-propanyl)cyclohexanone, 1-methyl-4-(2-propanyl)-1,4-cyclohexadiene, 4-(2-methyl-2-propanyl)cyclohexanol, 2-(2-methyl-2-propanyl)cyclohexyl acetate, 4-(2-methyl-2-propanyl)cyclohexyl acetate, 1-methyl-4-(prop-1-en-2-yl)cyclohex-1-ene, 2-methyl-4-propyl-1,3-oxathiane, (3E)-3-methyl-4-(2,6,6-trimethyl-2-cyclohexan-1-yl)-3-buten-2-one, methyl 2,6,6-trimethyl-3-cyclohexene-1-carboxylate, (3E)-3-methyl-4-(2,6,6-trimethyl-2-cyclohexen-1-yl)-3-buten-2-one and (1E)-1-(2,6,6-trimethyl-2-cyclohexen-1-yl)-1-penten-3-one, 3-methyl-5-(2,2,3-trimethyl-3-cyclopenten-1-yl)-2-pentanol, 2-methylundecanal, 2,6-nonadienal, 2,6-nonadienol, nonanal, octanal, oct-2-en-4-one, oxacyclohexadecan-2-one, 1-oxa-12- and 13-cyclohexadecen-2-one, 1,1'-oxydibenzene, pentyl 2-hydroxybenzoate, 2-phenoxyethanol, 2-phenylacetaldehyde, 3-phenylbutanal, 2-phenylethanol, 2-phenylethyl acetate, phenylmethanol, 4-[(2-propanyl) cyclohexyl]methanol, 7-propyl-2H-benzo[b][1,4] dioxepin-3 (4H)-one, tetrahydro-2-isobutyl-4-methyl-4 (2H)-pyranol, 3a,6,6,9a-tetramethyldodecahydronaphtho[2,1-b]furan, 1-(3,6,8,8-tetramethyl-2,3,4,7,8,8a-hexahydro-1H-3a,7-methanoazulen-5-yl) ethan-1-one, 2,3,6,7- and 2,4,6,8-tetramethylnonan-1-ol, 3,6,8,8-tetramethyloctahydro-1H-3a, 7-methanoazulen-6-yl acetate, 2,2,6,8-tetramethyl-1,2,3,4,4a,5,8,8a-octahydro-1-naphthalenol, 1-(2,3,8,8-tetramethyl-1,2,3,4,5,6,7,8-, 1,2,3,5,6,7,8,8a- and 1,2,3,4,6,7,8,8a-octahydronaphthalen-2-yl) ethan-1-one, tricyclo [5.2.1.0 (2,6)]dec-3- and 4-en-8-yl acetate, 2,2,2-trichloro-1-phenylethyl acetate, tricyclo[5.2.1.0 (2,6)]dec-3- or 4-en-8-yl propanoate, 1,7,7-trimethylbicyclo[2.2.1]heptan-2-ol, 1,7,7-trimethylbicyclo[2.2.1]heptan-2-one, 1,7,7-trimethylbicyclo[2.2.1]heptan-2-yl acetate, 2,6,6-trimethylbicyclo [3.1.1]hept-2-ene, 2-(1,7,7-trimetylbicyclo[2.2.1]hept-2-yl)-1-cyclohexanol, 2-, 3- and 4-(5,5,6-trimethylbicyclo[2.2.1] hept-2-yl)-1-cyclohexanol, (2E)-1-[2,6,6-trimethyl-1-cyclohexen-1-yl]-2-buten-1-one, (2E)-1-(2,6,6-trimethyl-2-cyclohexen-1-yl)-2-buten-1-one, (2E)-1-(2,6,6-trimethyl-3-cyclohexen-1-yl)-2-buten-1-one, 3,8,9-, 4,6,8- and 4,7,9-trimethyldecan-2-ol, 1,3,3-trimethyl-2-oxabicyclo[2.2.2] octane, 2,2,5-trimethyl-5-pentylcyclopentanone, 2,6,6-trimethylspiro[bicyclo[3.1.1]heptane-3,1'-cyclohexane]-2'-en-4'-one, undecanal, 1,3,5-undecatriene and 10-undecenal.

15. The perfume system according to claim 5, wherein the perfumery raw material of Group A is selected from the group consisting of allyl 2-(cyclohexyloxy)acetate, allyl 3-cyclohexylpropanoate, allyl heptanoate, allyl hexanoate, benzaldehyde, benzyl acetate, benzyl benzoate, benzyl 2-hydroxybenzoate, 2-cyclohexylethyl acetate, cyclohexyl 2-hydroxybenzoate, 4-cyclohexyl-2-methyl-2-butanol, decanal, diethyl 1,4-cyclohexanedicarboxylate, (2,2-dimethoxyethyl) benzene, 6,6-dimethoxy-2,5,5-trimethyl-2-hexene, 2-(6,6-dimethylbicyclo[3.1.1]hept-2-en-2-yl)ethyl acetate, 2,4-dimethyl-3-cyclohexene-1-carbaldehyde, 1-(5,5-dimethyl-1-cyclohexen-1-yl)-4-penten-1-one, 2,6-dimethyl-2-heptanol, 2,6-dimethyl-5-heptenal, 6,6-dimethyl-2-methylenebicyclo [3.1.1]heptane, 3,7-dimethyl-2,6- and 3,6-nonadienenitrile, 3,7-dimethyl-1,6-nonadien-3-ol, 3,7-dimethyl-2,6-octadienal, (E)-3,7-dimethyl-2,6-octadienol, (Z)-3,7-dimethyl-2,6-octadienol, 3,7-dimethyl-1,6-octadien-3-ol, 3,7-dimethyl-2,6-octadienyl acetate, 3,7-dimethyl-3-octanol, 3,7-dimethyl-6-octenenitrile, 3,7-dimethyl-6-octen-1-ol, 2,6-dimethyl-7-octen-2-ol, 3,7-dimethyl-6-octenyl acetate, 1,1-dimethyl-2-phenylethyl butanoate, 1,1-dimethyl-2-phenylethyl acetate, 3,3-dimethyl-5-[2,2,3-trimethyl-3-cyclopenten-1-yl]-4-penten-2-ol, 1,4-dioxacycloheptadecane-5,17-dione, dodecanal, dodecanol, (Z)-4-dodecenal, ethyl butanoate, ethyl 3-hydroxybut-2-enoate, ethyl 2-methylbutanoate, ethyl 2-methyl-1,3-dioxolane-2-acetate, ethyl 2-methylpentanoate, ethyl 3-oxobutanoate, 3-(2- and 4-ethylphenyl)-2,2-dimethylpropanal, (2E)-2-ethyl-4-[2,2,3-trimethyl-3-cyclopenten-1-yl]-2-buten-1-ol, 6-ethyl-2,10,10-trimethyl-1-oxaspiro[4.5]deca-3,6-diene, 5-heptyldihydro-2 (3H)-furanone, 4,6,6,7,8,8-hexamethyl-1,3,4,6,7,8-hexahydrocyclopenta[g] isochromene, 1-(3,5,5,6,8,8-hexamethyl-5,6,7,8-tetrahydro-2-naphthalenyl) ethanone, (Z)-3-hexen-1-ol, (Z)-3-hexenyl acetate, (Z)-3-hexenyl 2-hydroxybenzoate, hexyl acetate, 5-hexyldihydrofuran-2 (3H)-one, hexyl 2-hydroxybenzoate, hexyl 2-methylpropanoate, 3- and 4-(4-hydroxy-4-methylpentyl)-3-cyclohexene-1-carbaldehyde, 1-isopropyl-4-methylbenzene, 2-isopropyl-5-methylcyclohexan-1-ol, isopropyl 2-methylbutanoate, 4-isopropyl-1-methylcyclohexyl acetate, 3-(3-isopropyl-1-phenyl) butanal, 3-(4-isopropylphenyl)-2-methylpropanal, isopropyl tetradecanoate, 4-methoxybenzaldehyde, 1-methoxy-4-methylbenzene, 3-(4-methoxyphenyl)-2-methylpropanal, 4-(2-methoxy-2-propanyl)-1-methylcyclohexene, 1-methoxy-4-(2-propenyl) benzene, 6-methoxy-3,6,8,8-tetramethyloctahydro-1H-3a,7-methanoazulene, methyl benzoate, 7-methyl-2H-1,5-benzodioxepin-3 (4H)-one, 3-methyl-2-buten-1-yl acetate, 2- and 3-methylbutyl acetate, 2- and 3-methylbutyl butyrate, 2-methylbutyl 2-hydroxybenzoate, 2-(4-methylcyclohex-3-enyl) propan-2-ol, 2-(4-methyl-3-cyclohexen-1-yl)-2-propanyl acetate, 2-{2-[4-methyl-3-cyclohexen-1-yl] propyl}cyclopentanone, (E)-4-methyl-3-decen-5-ol, methyl 2,2-dimethyl-6-methylidenecyclohexanecarboxylate, methyl 2,4-dihydroxy-3,6-dimethylbenzoate, 5-methylheptan-3-one oxime, methyl 7-isopropyl-1,4a-dimethyl-1,2,3,4,4a,4b,5,6,7,8,10,10a-dodecahydrophenanthrene-1-carboxylate and methyl 7-isopropyl-1,4a-dimethyltetradecahydrophenanthrene-1-carboxylate, 1-methyl-4-(4-methyl-3-pentenyl)-3-cyclohexene-1-carbaldehyde, 2-methyl-3-[4-(2-methyl-2-propanyl)phenyl]propanal, 4-methyl-2-(2-methyl-1-propen-1-yl)tetrahydro-2H-pyran, methyl 2-octynoate, methyl 2-(3-oxo-2-pentylcyclopentyl)acetate, 4-methyl-4-penten-2-yl 2-methylpropanoate, 3-methyl-5-phenyl-1-pentanol, 5-methyl-2-(2-propanyl)cyclohexanone, 1-methyl-4-(2-propanyl)-1,4-cyclohexadiene, 4-(2-methyl-2-propanyl)cyclohexanol, 2-(2-methyl-2-propanyl)cyclohexyl acetate, 4-(2-methyl-2-propanyl)cyclohexyl acetate, 1-methyl-4-(prop-1-en-2-yl)cyclohex-1-ene, 2-methyl-4-propyl-1,3-oxathiane, (3E)-3-methyl-4-(2,6,6-trimethyl-2-cyclohexan-1-yl)-3-buten-2-one, methyl 2,6,6-trimethyl-3-cyclohexene-1-carboxylate, (3E)-3-methyl-4-(2,6,6-trimethyl-2-cyclohexen-1-yl)-3-buten-2-one and (1E)-1-(2,6,6-trimethyl-2-cyclohexen-1-yl)-1-penten-3-one, 3-methyl-5-(2,2,3-trimethyl-3-cyclopenten-1-yl)-2-pentanol, 2-methylundecanal, 2,6-nonadienal, 2,6-nonadienol, nonanal, octanal, oct-2-en-4-one, oxacyclohexadecan-2-one, 1-oxa-12- and 13-cyclohexadecen-2-one, 1,1'-oxydibenzene, pentyl 2-hydroxybenzoate, 2-phenoxyethanol, 2-phenylacetaldehyde, 3-phenylbutanal, 2-phenylethanol, 2-phenylethyl acetate, phenylmethanol, 4-[(2-propanyl) cyclohexyl]methanol, 7-propyl-2H-benzo[b][1,4] dioxepin-3 (4H)-one, tetrahydro-2-isobutyl-4-methyl-4 (2H)-pyranol, 3a,6,6,9a-tetramethyldodecahydronaphtho[2,1-b]furan, 1-(3,6,8,8-tetramethyl-2,3,4,7,8,8a-hexahydro-1H-3a,7-methanoazulen-5-yl) ethan-1-one, 2,3,6,7- and 2,4,6,8-tetramethylnonan-1-ol, 3,6,8,8-tetramethyloctahydro-1H-3a,7-methanoazulen-6-yl acetate, 2,2,6,8-tetramethyl-1,2,3,4,4a,5,8,8a-octahydro-1-naphthalenol, 1-(2,3,8,8-tetramethyl-1,2,3,4,5,6,7,8-, 1,2,3,5,6,7,8,8a- and 1,2,3,4,6,7,8,8a-octahydronaphthalen-2-yl) ethan-1-one, tricyclo [5.2.1.0 (2,6)]dec-3- and 4-en-8-yl acetate, 2,2,2-trichloro-1-phenylethyl acetate, tricyclo[5.2.1.0 (2,6)]dec-3- or 4-en-8-yl propanoate, 1,7,7-trimethylbicyclo[2.2.1]heptan-2-ol, 1,7,7-trimethylbicyclo[2.2.1]heptan-2-one, 1,7,7-trimethylbicyclo[2.2.1]heptan-2-yl acetate, 2,6,6-trimethylbicyclo [3.1.1]hept-2-ene, 2-(1,7,7-trimetylbicyclo[2.2.1]hept-2-yl)-1-cyclohexanol, 2-, 3- and 4-(5,5,6-trimethylbicyclo[2.2.1] hept-2-yl)-1-cyclohexanol, (2E)-1-[2,6,6-trimethyl-1-cyclohexen-1-yl]-2-buten-1-one, (2E)-1-(2,6,6-trimethyl-2-cyclohexen-1-yl)-2-buten-1-one, (2E)-1-(2,6,6-trimethyl-3-cyclohexen-1-yl)-2-buten-1-one, 3,8,9-, 4,6,8- and 4,7,9-trimethyldecan-2-ol, 1,3,3-trimethyl-2-oxabicyclo[2.2.2] octane, 2,2,5-trimethyl-5-pentylcyclopentanone, 2,6,6-trimethylspiro[bicyclo[3.1.1]heptane-3,1'-cyclohexane]-2'-en-4'-one, undecanal, 1,3,5-undecatriene and 10-undecenal.

* * * * *